(12) United States Patent
Jeong et al.

(10) Patent No.: US 12,419,584 B2
(45) Date of Patent: Sep. 23, 2025

(54) ELECTROCARDIOGRAM DATA PROCESSING SERVER, METHOD FOR CALCULATING EXPECTED ANALYSIS TIME REQUIRED FOR ELECTROCARDIOGRAM ANALYSIS, AND COMPUTER PROGRAM THEREFOR

(71) Applicant: ATSENS CO., LTD., Gyeonggi-do (KR)

(72) Inventors: Jong Ook Jeong, Gyeonggi-do (KR); Chang Ho Lee, Gyeonggi-do (KR); Kab Mun Cha, Gyeonggi-do (KR); Jin A Lee, Gyeonggi-do (KR)

(73) Assignee: ATSENS CO., LTD., Gyeonggi-Do (KR)

( * ) Notice: Subject to any disclaimer, the term of this patent is extended or adjusted under 35 U.S.C. 154(b) by 451 days.

(21) Appl. No.: 17/857,225

(22) Filed: Jul. 5, 2022

(65) Prior Publication Data
US 2023/0111726 A1    Apr. 13, 2023

(30) Foreign Application Priority Data
Oct. 13, 2021    (KR) .......................... 10-2021-0135938

(51) Int. Cl.
| | | |
|---|---|---|
| *A61B 5/318* | (2021.01) | |
| *A61B 5/00* | (2006.01) | |
| *G16H 50/20* | (2018.01) | |

(52) U.S. Cl.
CPC .......... *A61B 5/7264* (2013.01); *G16H 50/20* (2018.01); *A61B 5/0006* (2013.01); *A61B 5/318* (2021.01)

(58) Field of Classification Search
CPC ....... A61B 5/7264; A61B 5/318; A61B 5/346; A61B 5/0006; G16H 50/20
See application file for complete search history.

(56) References Cited

U.S. PATENT DOCUMENTS

| | | | | |
|---|---|---|---|---|
| 2004/0122787 A1* | 6/2004 | Avinash | ................. | A61B 5/395 |
| | | | | 706/50 |
| 2017/0188932 A1* | 7/2017 | Singer | .................... | G16H 50/70 |
| 2023/0162857 A1* | 5/2023 | Lee | ...................... | A61B 5/0008 |
| | | | | 600/549 |

FOREIGN PATENT DOCUMENTS

| | | | |
|---|---|---|---|
| JP | 2006511882 A | 4/2006 | |
| JP | 2017148364 A | 8/2017 | |

(Continued)

*Primary Examiner* — Eric D. Bertram
(74) *Attorney, Agent, or Firm* — Bridgeway IP Law Group, PLLC; Sang Ho Lee; Hyun Woo Shin

(57) ABSTRACT

Disclosed is a method of generating and processing analysis data regarding electrocardiogram signals of a target object. The method includes receiving an electrocardiogram signal of a target object and a first classification data regarding the electrocardiogram signal of the target object. The method further includes calculating statistical data in consideration of a past medical history and symptom information at time of measurement of the target object, generating a second classification data by applying the statistical data to the electrocardiogram signal of the target object, determining a section of interest to be analyzed in consideration of the electrocardiogram signal and the second classification data, extracting signal sections corresponding to the section of interest to be analyzed from the second classification data regarding the electrocardiogram signal, calculating an expected analysis time for the signal sections, and transmitting analysis data regarding the signal sections to an analyst terminal.

12 Claims, 18 Drawing Sheets

(56) References Cited

FOREIGN PATENT DOCUMENTS

| KR | 1020120113985 A | 10/2012 |
| KR | 1020180113511 A | 10/2018 |
| KR | 1020200004722 A | 1/2020 |
| KR | 102134206 B1 | 7/2020 |
| KR | 1020200109233 A | 9/2020 |

\* cited by examiner

FIG. 15

| LABEL_P | DAY | START | DURATION | END |
|---|---|---|---|---|
| AFIB_1 | 1 | 4:00:00 | 0:00:35 | 4:00:35 |
| AFIB_1 | 3 | 8:00:00 | 0:11:00 | 8:11:00 |
| AFIB_1 | 3 | 8:15:00 | 0:08:40 | 8:23:40 |
| AFIB_1 | 3 | 8:24:00 | 0:08:10 | 8:32:10 |
| AFIB_1 | 3 | 8:35:00 | 0:05:33 | 8:40:33 |
| AFIB_1 | 3 | 8:43:30 | 0:07:50 | 8:51:20 |
| AFIB_1 | 3 | 10:10:00 | 0:00:12 | 10:10:12 |
| AFIB_1 | 3 | 13:10:00 | 0:07:10 | 13:17:10 |
| AFIB_1 | 3 | 13:30:00 | 0:05:40 | 13:35:40 |
| AFIB_1 | 3 | 13:38:00 | 0:07:55 | 13:45:55 |
| AFIB_1 | 3 | 13:45:00 | 0:05:31 | 13:50:31 |
| AFIB_1 | 3 | 13:55:00 | 0:05:30 | 14:00:30 |
| AFIB_1 | 3 | 15:15:00 | 0:00:40 | 15:15:40 |
| AFIB_1 | 3 | 23:01:00 | 0:00:27 | 23:01:27 |
| AFIB_1 | 3 | 23:10:00 | 0:00:25 | 23:10:25 |
| AFIB_1 | 5 | 7:45:00 | 0:10:30 | 7:55:30 |
| AFIB_1 | 5 | 7:58:00 | 0:08:30 | 8:06:30 |
| AFIB_1 | 5 | 8:08:20 | 0:06:55 | 8:15:15 |
| AFIB_1 | 5 | 8:17:00 | 0:06:49 | 8:23:49 |
| AFIB_1 | 5 | 8:25:10 | 0:06:34 | 8:31:44 |
| AFIB_1 | 5 | 12:55:00 | 0:08:10 | 13:03:10 |
| AFIB_1 | 5 | 13:05:00 | 0:07:40 | 13:12:40 |
| AFIB_1 | 5 | 13:14:00 | 0:07:30 | 13:21:30 |
| AFIB_1 | 5 | 13:22:00 | 0:07:28 | 13:29:28 |
| AFIB_1 | 5 | 13:32:00 | 0:07:10 | 13:37:10 |
| AFIB_2 | 7 | 8:10:00 | 0:01:10 | 8:11:10 |
| AFIB_2 | 7 | 8:11:00 | 0:00:15 | 8:11:15 |
| AFIB_2 | 7 | 8:13:00 | 0:00:08 | 8:13:08 |
| AFIB_2 | 9 | 8:00:00 | 0:00:10 | 8:00:10 |
| AFIB_1 | 11 | 8:11:00 | 0:09:40 | 8:20:40 |
| AFIB_1 | 11 | 8:22:00 | 0:07:10 | 8:29:10 |

FIG. 16

| LABEL_P | FREQUENCY |
|---------|-----------|
| AFIB_1  | 27        |
| AFIB_2  | 4         |

ELECTROCARDIOGRAM DATA PROCESSING SERVER, METHOD FOR CALCULATING EXPECTED ANALYSIS TIME REQUIRED FOR ELECTROCARDIOGRAM ANALYSIS, AND COMPUTER PROGRAM THEREFOR

CROSS-REFERENCE TO RELATED APPLICATIONS

This application is based on and claims priority under 35 U.S.C. § 119 to Korean Patent Application No. 10-2021-0135938, filed on Oct. 13, 2021, in the Korean Intellectual Property Office, the disclosure of which is incorporated by reference herein in its entirety.

BACKGROUND

1. Field

One or more embodiments relate to an electrocardiogram data processing server, a method of generating and processing analysis data regarding electrocardiogram signals of a target object, and a computer program therefor.

2. Description of the Related Art

When the heart muscle contracts and relaxes, electrical depolarization and repolarization generate a potential difference. An electrocardiogram refers to the potential difference detected by attaching a surface electrode to the skin. The electrocardiogram has a size from dozens of $\mu V$ to several mV and a frequency band of less than 100 Hz.

To check a heart disease, it is necessary to measure the electrocardiogram for a certain period, and a doctor diagnoses the electrocardiogram measured in this way based on an analysis result by an analyst. It takes from 3 to 6 hours for an analyst to analyze an electrocardiogram measured in 24 hours, and, when time for measuring an electrocardiogram increases, time for analyzing the electrocardiogram may proportionally increase.

Also, an actual analysis of a requested analysis for an electrocardiogram may take longer or shorter than expected, and thus the fee to be paid to an analyst may differ from that for an actual analysis time.

Therefore, it is necessary to anticipate and control time needed for analysis of an electrocardiogram.

The related art stated above is technical information that the inventor possessed for the derivation of one or more embodiments or obtained in the process of derivation of one or more embodiments and may not necessarily be a known technique disclosed to the general public prior to the filing of one or more embodiments.

SUMMARY

One or more embodiments provide a method of processing electrocardiogram data.

Additional aspects will be set forth in part in the description which follows and, in part, will be apparent from the description, or may be learned by practice of the presented embodiments of the disclosure.

According to one or more embodiments, a method of generating and processing analysis data regarding electrocardiogram signals of a target object, the method includes receiving, by an electrocardiogram data processing server, an electrocardiogram signal of a target object; receiving, by the electrocardiogram data processing server, a first classification data regarding the electrocardiogram signal of the target object; calculating, by the electrocardiogram data processing server, statistical data in consideration of a past medical history and symptom information at the time of measurement of the target object and generating, by the electrocardiogram data processing server, a second classification data by applying the statistical data to the electrocardiogram signal of the target object; determining, by the electrocardiogram data processing server, an section of interest to be analyzed in consideration of the target object, the electrocardiogram signal, and the second classification data; extracting, by the electrocardiogram data processing server, signal sections corresponding to the section of interest to be analyzed from the second classification data regarding the electrocardiogram signal and calculating an expected analysis time for the signal sections; and transmitting analysis data regarding the signal sections to an analyst terminal.

The method may further include receiving a first label for a first signal section input by the analyst terminal or an analysis module; and, when label information for the first signal section included in the second classification data is not identical to the first label, re-extracting signal sections classified into a same category as the first signal section and generating third classification data by re-classifying the signal sections according to the first label.

The method may further include receiving a first priority value for a first signal section input by the analyst terminal or an analysis module; and generating third classification data by re-classifying signal sections classified into the same category as the first signal section included in the second classification data by setting the first priority value thereto.

The method may further include receiving an abnormal signal marker for a first signal section input by the analyst terminal or an analysis module; and re-extracting signal sections classified into a same category as the first signal section included in the second classification data and generating third classification data by re-classifying the signal sections according to the abnormal signal marker.

The method may further include receiving a second priority value for a second label input by the analyst terminal or an analysis module; and re-extracting signal sections classified according to a second label included in the second classification data and generating third classification data by re-classifying the signal sections according to the second priority value.

The method may further include receiving an input for excluding a second signal section input by the analyst terminal or an analysis module from the section of interest to be analyzed, transmitting a confirmation request regarding the section of interest to be analyzed from which the second signal section is excluded to a medical staff terminal, and requesting an approval reply to the medical staff terminal.

The method may further include transmitting a confirmation request regarding the third classification data to which data received from the analyst terminal or the analysis module is applied to a medical staff terminal and requesting an approval reply to the medical staff terminal.

In the calculating of the expected analysis time, when it is determined that the expected analysis time is equal to or greater than a pre-set reference value, the generating of the second classification data and the determining of the section of interest to be analyzed may be performed again.

According to one or more embodiments, an electrocardiogram data processing server includes a processor; a computer readable memory; and a communication unit, wherein the processor receives an electrocardiogram signal of a target object, receives first classification data regarding the electrocardiogram signal of the target object, calculates statistical data in consideration of a past medical history and symptom information at a time of measurement of the target object, generates second classification data regarding the electrocardiogram signal by applying the statistical data to the electrocardiogram signal of the target object, determines a section of interest to be analyzed in consideration of the target object, the electrocardiogram signal, and the second classification data, extracts signal sections corresponding to the section of interest to be analyzed from the second classification data regarding the electrocardiogram signal and calculates an expected analysis time for the signal sections corresponding to the section of interest to be analyzed, and transmits analysis data regarding the signal sections corresponding to the section of interest to be analyzed to an analyst terminal.

According to one or more embodiments, there is provided a computer program stored in a computer-readable storage medium to execute any one of methods by using a computer.

According to one or more embodiments, there is provided another method for implementing one or more embodiments, another system for implementing one or more embodiments, and a computer-readable recording medium having recorded thereon a computer program for executing the method.

Other aspects, features, and advantages will become apparent from the following drawings, claims, and detailed description of the invention.

According to one or more embodiments, an expected analysis time for an analyst to analyze an electrocardiogram signal may be calculated.

BRIEF DESCRIPTION OF THE DRAWINGS

The above and other aspects, features, and advantages of certain embodiments of the disclosure will be more apparent from the following description taken in conjunction with the accompanying drawings, in which:

FIG. 15 is a diagram showing sections to be analyzed corresponding to analysis conditions.

FIG. 16 is a diagram showing occurrence frequencies of a first label and a second label in the sections to be analyzed of FIG. 15.

DETAILED DESCRIPTION

Figure 1:
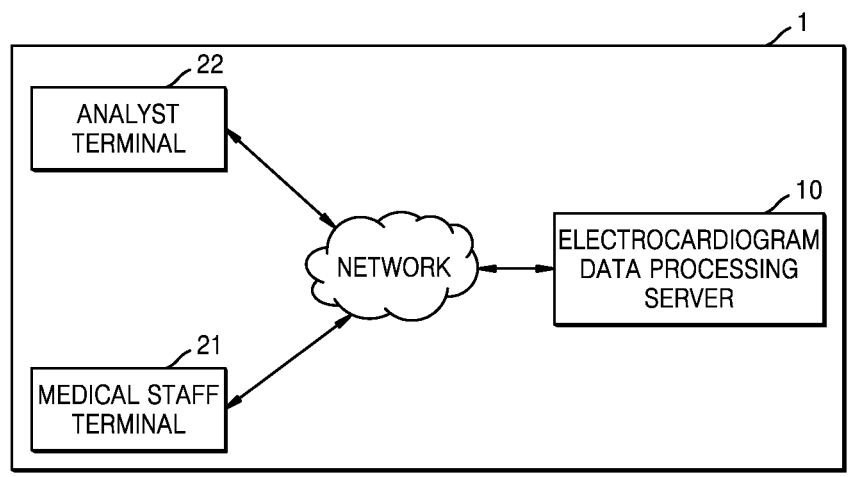
FIG. 1 is a diagram showing a network environment of an electrocardiogram data processing system according to one or more embodiments.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

Hereinafter, the configuration and operation of one or more embodiments will be described in detail with reference to embodiments of one or more embodiments shown in the accompanying drawings.

One or more embodiments may include various embodiments and modifications, and embodiments thereof will be illustrated in the drawings and will be described herein in detail. The effects and features of one or more embodiments and the accompanying methods thereof will become apparent from the following description of the embodiments, taken in conjunction with the accompanying drawings. However, one or more embodiments are not limited to the embodiments described below, and may be embodied in various modes.

Reference will now be made in detail to embodiments, examples of which are illustrated in the accompanying drawings. In the drawings, the same elements are denoted by the same reference numerals, and a repeated explanation thereof will not be given.

In this specification, terms such as "learning" are not intended to refer to human mental processes such as educational activities, but should be interpreted as terms referring to performing machine learning through computing according to procedures.

It will be understood that although the terms "first", "second", etc. may be used herein to describe various elements, these elements should not be limited by these terms. These elements are only used to distinguish one element from another.

As used herein, the singular forms "a," "an" and "the" are intended to include the plural forms as well, unless the context clearly indicates otherwise.

It will be further understood that the terms "comprises" and/or "comprising" used herein specify the presence of stated features or components, but do not preclude the presence or addition of one or more other features or components.

Sizes of elements in the drawings may be exaggerated for convenience of explanation. In other words, since sizes and thicknesses of components in the drawings are arbitrarily illustrated for convenience of explanation, the following embodiments are not limited thereto.

When a certain embodiment may be implemented differently, a specific process order may be performed differently from the described order. For example, two consecutively described processes may be performed substantially at the same time or performed in an order opposite to the described order.

According to one or more embodiments, a network refers to a connection established (or formed) using all communication methods and may refer to a communication network connected through all communication methods for transmitting and receiving data between a terminal and a terminal or between a terminal and a server.

All communication methods may include all communications through predetermined communication standards, predetermined frequency bands, predetermined protocols, or predetermined channels. For example, all communication methods may include Bluetooth, BLE, Wi-Fi, Zigbee, 3G, LTE, an ultrasound communication method, etc., and may include all short-distance communication, long-distance communication, wireless communication, and wired communication. Of course, it is not limited to the above examples.

According to one or more embodiments, a short-distance communication method may refer to a communication method in which communication is possible only when devices (terminals or servers) performing communication are within a certain range, e.g., Bluetooth, NFC, etc. A long-distance communication method may refer to a communication method in which devices performing communication may communicate regardless of a distance therebetween. For example, the long-distance communication method may refer to a method in which two devices performing communication through a repeater like an AP may communicate even when a distance therebetween is greater than a certain distance and may include communication methods using cellular networks (3G, LTE, etc.) like SMS and phone calls. Of course, it is not limited to the above examples. Reception of an online activity using a network may mean that communication may be performed between a server and a terminal through all communication methods.

FIG. 1 is a diagram showing a network environment of an electrocardiogram data processing system 1 according to one or more embodiments.

Figure 11:
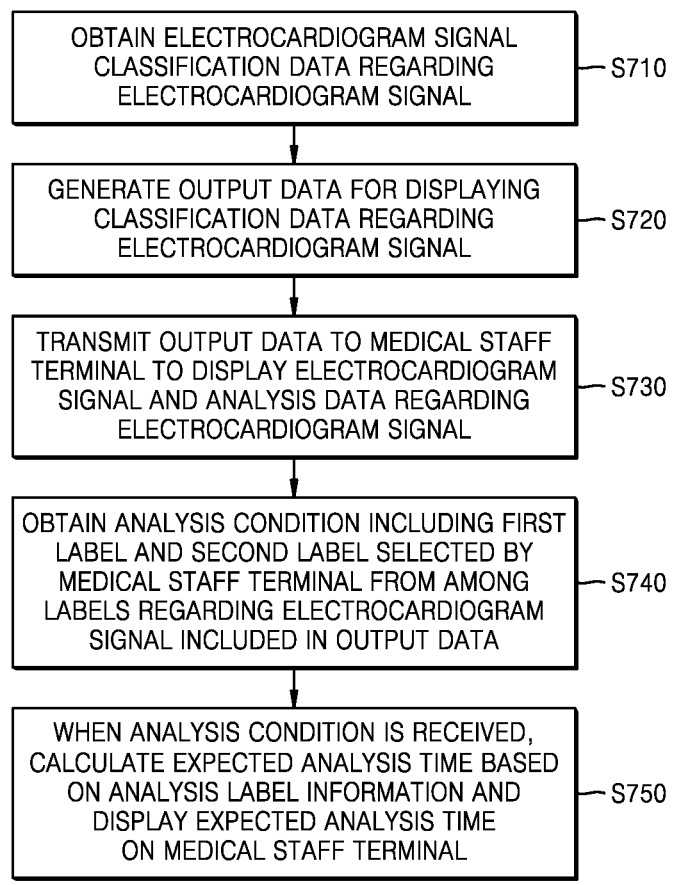
FIG. 11 is a flowchart of a method of calculating an expected analysis time based on an analysis condition input as a label according to one or more embodiments.

The electrocardiogram data processing system 1 relates to electrocardiogram signals and a system for processing classification data for electrocardiogram signals and may analyze electrocardiogram signals and generate labels related to heart rates and/or electrocardiogram signals. Here, the label may be generated as shown in FIG. 11.

The electrocardiogram data processing system 1 may generate labels classified according to pre-set category values with respect to electrocardiogram signals, which are signals related to the heart. Such data including labels may be referred to as classification data.

The electrocardiogram data processing server 10 may be implemented to obtain electrocardiogram signals and label information for the electrocardiogram signals and to execute an additional analysis process therefor. The electrocardiogram data processing server 10 may calculate an expected analysis time for electrocardiogram signals based on labels for the electrocardiogram signals and analysis conditions of a medical staff. An algorithm for calculating an expected analysis time is generated by using a certain method and may be generated by using methods such as machine learning, reinforcement learning, supervised learning, and unsupervised learning. The algorithm for calculating an expected analysis time may be updated based on input data. Therefore, it is possible to know the time required to analyze electrocardiogram data by calculating an expected analysis time in advance before analyzing the electrocardiogram data. Therefore, a medical staff may know in advance the time and cost needed to analyze electrocardiogram data. An analyst may also analyze electrocardiogram data with the knowledge of an expected analysis time and schedule a work process regarding expected analysis time for one or more pieces of electrocardiogram data in advance. An electrocardiogram data processing server 10 may provide data regarding a calculated expected analysis time to a medical staff terminal 21, receive modified analysis conditions from the medical staff terminal 21, re-calculate an expected analysis time according to the modified analysis conditions, and generate data regarding the expected analysis time. When a confirmation request regarding analysis conditions is received from the medical staff terminal 21, the electrocardiogram data processing server 10 may transmit an analysis request according to the analysis conditions to an analyst terminal 22, such that an analyst executes a process of analysis for sections of an electrocardiogram signal. Through this, the medical staff may check an expected analysis time and, when it is determined that the expected analysis time is too long, may change analysis conditions to reduce the expected analysis time. On the other hand, when the expected analysis time is shorter than a pre-set value, the analysis conditions may be changed to analyze more signal sections.

In another embodiment, when a desired expected analysis time is received by a medical staff or an analyst, analysis conditions corresponding to the desired expected analysis time may be determined and data regarding the analysis condition may be transmitted to a terminal of the medical staff or the analyst. The data (or parameters) regarding the analysis condition may include signal segments corresponding to the analysis condition and the expected analysis time required to analyze the signal segments. The electrocardiogram data processing server 10 may return analysis conditions for the desired expected analysis time by using a model machine-learned by using analysis conditions and analysis times needed to analyze electrocardiogram signals according to the analysis conditions and functions.

The electrocardiogram data processing server 10 may extract interval sections from an electrocardiogram signal and extract label corresponding to each section of the electrocardiogram signal (e.g., peak points, signal slopes, signal widths) by using morphology within the interval sections. The electrocardiogram data processing server 10 may execute a classification process of adding labels corresponding to respective sections of an electrocardiogram signal. The classification process is based on a certain algorithm, and the corresponding algorithm may be generated through learning by various machine learning, reinforcement learning algorithms, and neural networks. The corresponding algorithm may be changed to an algorithm having a higher prediction probability when an amount of input data is increased.

The electrocardiogram data processing server 10 causes an electrocardiogram signal and label information regarding the electrocardiogram signal to be displayed on an output unit of the medical staff terminal 21, the analyst terminal 22, and other user terminals connected to the electrocardiogram data processing server 10. Although FIG. 1 shows one medical staff terminal and one analyst terminal, one or more embodiments are not limited thereto, and the electrocardiogram data processing server 10 may be connected to and communicate with a plurality of medical staff terminals and/or a plurality of analyst terminals. The electrocardiogram data processing server 10 may be implemented in one computing device or may be implemented in a distributed manner with a plurality of computing devices.

The electrocardiogram data processing server 10 may generate an electrocardiogram analysis data according to analysis conditions from a plurality of medical staff terminals. The electrocardiogram data processing server 10 may cause one analyst terminal 22 selected from among a plurality of analyst terminals to generate an electrocardiogram analysis data according to analysis conditions. Here, the analysis condition is for selecting signal segments to be analyzed from among the electrocardiogram signals, and one or more values or morphological characteristics such as a label, data value, signal interval, signal interval, pulse rate, respiration rate, and signal to be analyzed may contain itself. The electrocardiogram analysis data may include data analyzed in response to an analysis condition among electrocardiogram signals.

Here, for convenience of explanation, a method of storing the electrocardiogram data stored in the electrocardiogram data processing server 10 is omitted. However, it is obvious that electrocardiogram data may be stored via a wire or wirelessly by an electrocardiogram measuring person or a medical staff or may be automatically stored by an electrocardiogram measuring device.

According to one or more embodiments, the electrocardiogram data processing server 10 may calculate an expected analysis time based on an electrocardiogram signal and classification data regarding the electrocardiogram signal. The electrocardiogram data processing server 10 may calculate a first analysis time for each section of an electrocardiogram signal. The electrocardiogram data processing server 10 may calculate an expected analysis time for the electrocardiogram signal based on calculated first analysis times. The electrocardiogram data processing server 10 may extract noise sections included in the electrocardiogram signal, calculate a second analysis time for the noise sections based on signal lengths of the noise sections, and add the second analysis time thereto to calculate an expected analysis time. The electrocardiogram data processing server 10 may determine a section of interest, which is a portion of the electrocardiogram signal, select data of interest of the electrocardiogram signal corresponding to the section of interest, and calculate an expected analysis time regarding the data of interest. The section of interest may be determined in an electrocardiogram signal based on questionnaires input by a patient, classification data regarding the corresponding electrocardiogram signal, analysis conditions input by a medical staff or an analyst, etc. Here, the section of interest may include a section of the electrocardiogram signal measured at a specified period and time. The section of interest may refer to a section designated by various conditions. For example, the section of interest may be determined as one or more days (one day is 24 hours) determined in a measurement period during which an electrocardiogram signal is measured. The processor 120 may determine whether the expected analysis time is less than a pre-set target time. When the expected analysis time is less than the target time, the electrocardiogram signal may be transmitted to and analyzed by an analyst terminal. Here, the expected analysis time relates to time needed to analyze the electrocardiogram signal and may be calculated by various algorithms. Here, the desired expected analysis time is a time for analyzing the electrocardiogram signal and may be determined by an internal algorithm of a server or an algorithm of an external device or based on a value input by another device (a medical staff terminal, an analyst terminal, etc.). The electrocardiogram data processing server 10 may calculate an expected analysis time in consideration of the analysis conditions from classification data regarding the electrocardiogram signal. The analysis condition may be modified by the medical staff terminal. The electrocardiogram data processing server 10 may transmit result data regarding whether the expected analysis time is less than a pre-set target time to the medical staff terminal. The classification data regarding the electrocardiogram signal may be generated by classifying sections of the electrocardiogram signal by using the labels defined in FIG. 11, but one or more embodiments are not limited thereto.

The medical staff terminal 21 may access the electrocardiogram data processing server 10 and input an analysis condition regarding a registered electrocardiogram signal. The medical staff terminal 21 may receive an expected analysis time according to the analysis condition. The electrocardiogram analysis data may refer to data obtained by analyzing signal sections corresponding to analysis conditions. The medical staff terminal 21 may confirm the expected analysis time and re-enter an input for modifying the analysis condition. The medical staff terminal 21 may receive electrocardiogram analysis data analyzed according to an input analysis condition. The medical staff terminal 21 may receive a report on data according to the analysis condition.

The analyst terminal 22 may access the electrocardiogram data processing server 10 and input classification data regarding the electrocardiogram signal. The electrocardiogram data processing server 10 may provide interface data for inputting analysis data and may periodically provide input analysis data to the medical staff terminal 21 having a certain authority.

The electrocardiogram data processing system 1 may be connected to the analyst terminal 22 and the medical staff terminal 21 through a network and transmit/receive data to/from them.

Figure 2:
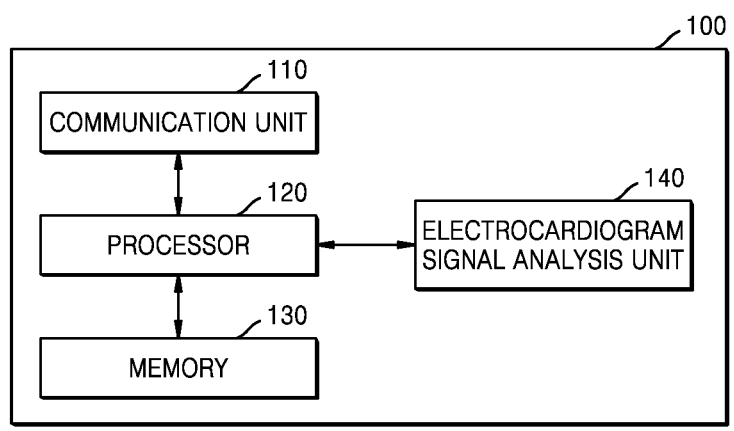
FIG. 2 is a block diagram of the electrocardiogram data processing server according to one or more embodiments.

FIG. 2 is a block diagram of the electrocardiogram data processing server 100 according to one or more embodiments.

The electrocardiogram data processing server 100 may include a communication unit 110, a processor 120, a memory 130, and an electrocardiogram signal analysis unit 140. The electrocardiogram data processing server 10 of FIG. 1 may be replaced with the electrocardiogram data processing server 100 of FIG. 2. The electrocardiogram data processing server 10 of FIG. 1 may have the same structure as the electrocardiogram data processing server 100. However, not all of the components shown in FIG. 2 may be essential components of the electrocardiogram data processing server 100. The electrocardiogram data processing server 100 may be implemented by more components than the components shown in FIG. 2 or fewer components than the components shown in FIG. 2. The electrocardiogram data processing server 100 may be a user terminal, a server, a system, or a separate device. Also, the electrocardiogram data processing server 100 may be implemented as a cloud system. When the electrocardiogram data processing server 100 is implemented as a cloud system, an analyst and a medical staff may be at the same location or at different locations, respectively.

The processor 120 typically controls the overall operation of the electrocardiogram data processing server 100. For example, the processor 120 may control the components included in the electrocardiogram data processing server 100 overall by executing a program stored in the electrocardiogram data processing server 100.

According to one or more embodiments, the processor 120 may calculate an expected analysis time using an electrocardiogram signal and classification data regarding the electrocardiogram signal. For example, the processor 120 may calculate the expected analysis time by using the analysis time required to verify the signal of the first label among the classification data. The processor 120 may calculate a first analysis time for each section of an electrocardiogram signal. The processor 120 may calculate an expected analysis time for the electrocardiogram signal based on calculated first analysis times. The processor 120 may extract noise sections included in the electrocardiogram signal, calculate a second analysis time for the noise sections based on signal lengths of the noise sections, and modify the second analysis time thereto to calculate the expected analysis time. The processor 120 may determine a section of interest. By selecting data of interest of the electrocardiogram signal corresponding to the section of interest, the expected analysis time regarding the data of interest may be re-calculated. The section of interest may be determined as one or more days determined in a measurement period during which an electrocardiogram signal is measured. The processor 120 may determine whether the expected analysis time is less than a pre-set target time. Here, the expected analysis time relates to time needed to analyze the electrocardiogram signal and may be calculated by various algorithms. Here, the desired expected analysis time is a time for analyzing the electrocardiogram signal and may be determined by an internal algorithm of a server or an algorithm of an external device or based on a value input by another device. The processor 120 may calculate an expected analysis time in consideration of the analysis conditions from classification data regarding the electrocardiogram signal. The processor 120 may transmit result data regarding whether the expected analysis time is less than a pre-set target time to the medical staff terminal. The processor 120 transmits the result data of comparing the expected analysis time with the target time to the medical staff terminal, so that the analysis condition and the section of interest are modified so that the analysis is completed in less than the target time.

According to one or more embodiments, the processor 120 may receive an analysis condition regarding the electrocardiogram signal from a medical staff terminal. The processor 120 may extract sections corresponding to the analysis condition and calculate an expected analysis time of the sections corresponding to the analysis condition in consideration of the occurrence pattern of the corresponding sections and analysis times for the corresponding sections.

The processor 120 may provide classification data regarding the electrocardiogram signal to a user terminal and input an analysis condition based on a section signal for the provided classification data. The classification data regarding the electrocardiogram signal may include an electrocardiogram signal, a heart rate of the electrocardiogram signal, category values for respective sections of the electrocardiogram signal, labels for the respective category values, etc. Category values and labels for the category values may be as shown in FIG. 11. The analysis condition may be set to one or more labels or to a particular time interval. The analysis condition may be input as a disease and may be changed to one or more labels.

The processor 120 may transmit an analysis request signal for the electrocardiogram signal to the analyst terminal and control the analyst terminal to input an analysis comment on the electrocardiogram signal. The analysis request signal may include sections regarding the analysis condition from among sections of the electrocardiogram signal. The analysis request signal may be generated and transmitted according to an approval signal for an analysis request from the medical staff terminal. The processor 120 may analyze sections for an analysis condition of a pre-stored default value. The default value may be a value predetermined in advance. An approval signal for the analysis request may be made without additional input from the medical staff.

The processor 120 is configured to control the electrocardiogram data processing server 100 overall. In detail, the processor 120 controls the overall operation of the electrocardiogram data processing server 100 by using various programs stored in a storage medium of the electrocardiogram data processing server 100. For example, the processor 120 may include a CPU, a RAM, a ROM, and a system bus. Here, the ROM is a component in which an instruction set for system booting is stored. The CPU copies stored operating system (O/S) of the electrocardiogram data processing server 100 to the RAM according to instructions stored in the ROM and executes the O/S to boot the system. When the booting of the system is completed, the CPU may perform various operations by copying various stored applications to the RAM and executing them. Although it has been described above that the electrocardiogram data processing server 100 includes only one CPU, the electrocardiogram data processing server 100 may be implemented with a plurality of CPUs (or DSPs, SoCs, etc.).

According to one or more embodiments, the processor 120 may be implemented as a digital signal processor (DSP) processing digital signals, a microprocessor, or a time controller (TCON). However, one or more embodiments are not limited thereto, and the processor 120 may include at least one of or defined as a central processing unit (CPU), a micro controller unit (MCU), a micro processing unit (MPU), a controller, an application processor (AP), a communication processor (CP), and an ARM processor. Also, the processor 120 may be implemented as a system on chip (SoC) or a large scale integration (LSI) having a processing algorithm embedded therein or may be embodied as a field programmable gate array (FPGA).

According to one or more embodiments, the memory 130 may store a computer program including instructions executable by the processor 120 to perform operations herein including operations of the electrocardiogram signal analysis unit 140 and may store data input to the electrocardiogram data processing server 100 or output from the electrocardiogram data processing server 100. According to one or more embodiments, the memory 130 may store an electrocardiogram signal and classification data regarding the electrocardiogram signal. The memory 130 may store data regarding an input analysis condition. The memory 130 may store data needed to generate output data regarding an electrocardiogram signal.

According to one or more embodiments, the memory 130 may include a storage medium of at least one type from among a flash memory type, a hard disk type, a multimedia card micro type, a card type memory (e.g., an SD or XD memory, etc.), a random access memory (RAM), a static random access memory (SRAM), a read-only memory (ROM), an electrically erasable programmable read-only memory (EEPROM), a programmable read-only memory (PROM), a magnetic memory, a magnetic disk, and an optical disc. Also, according to one or more embodiments, programs stored in the memory 130 may be classified into a plurality of modules according to their functions.

According to one or more embodiments, the communication unit 110 may communicate with a device outside the processor 120. For example, the communication unit 110 may communicate with an external device, such as a user terminal or another server, under the control of the processor 120. Also, the communication unit 110 may obtain user information or an user input through communication with an external interface. The electrocardiogram data processing server 100 may be a cloud system, where a network by a communication unit may be an intranet/internet. Also, communication security and electrocardiogram signal security may be implemented in various ways.

Figure 3:
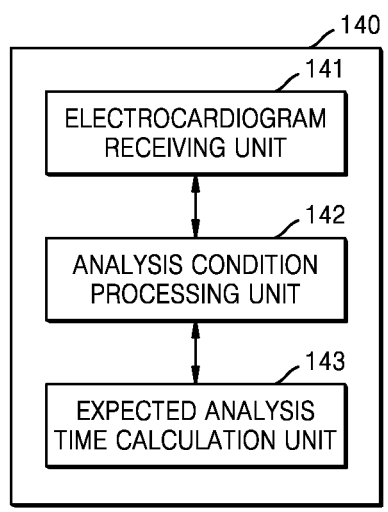
FIG. 3 is a block diagram of the electrocardiogram signal analysis unit according to one or more embodiments.

FIG. 3 is a block diagram of the electrocardiogram signal analysis unit 140 according to one or more embodiments.

The electrocardiogram signal analysis unit 140 may include an electrocardiogram receiving unit 141, an analysis condition processing unit 142, and an expected analysis time calculation unit 143.

The electrocardiogram receiving unit 141 may receive data regarding an electrocardiogram signal. The data regarding an electrocardiogram signal may include an electrocardiogram signal and classification data regarding the electrocardiogram signal. The data regarding the electrocardiogram signal may be data regarding an electrocardiogram signal measured for a certain period, e.g., one week or 14 days. Classification data regarding an electrocardiogram signal may include category values corresponding to respective signal waveforms of the electrocardiogram signal while displaying the signal waveforms in time series. The category values may be values converted into labels. The category values may include, but are not limited to, RR Pause, Bradycardia, NN delay, Heart Block, Atrial Fibrillation (AF), SVE, SVE tachycardia, R on T, VE tachycardia, VE run, PVC, Triplet (PVC), Couplet (PVC), Bigeminy (PVC) .), Ventricular Escape, etc. The category values may be converted into corresponding labels and included in analysis data regarding the electrocardiogram signal.

In another embodiment, the electrocardiogram receiving unit 141 may analyze signal waveforms of an electrocardiogram signal by using received data regarding the electrocardiogram signal and generate classification data regarding the electrocardiogram signal. The electrocardiogram receiving unit 141 may generate classification data regarding the electrocardiogram signal by dividing the electrocardiogram signal into signal segments according to signal waveforms and classifying the electrocardiogram signal by setting each signal segment to one of category values, thereby generating the classification data regarding the electrocardiogram signal.

The analysis condition processing unit 142 may transmit electrocardiogram output data for displaying the electrocardiogram signal and the classification data regarding the electrocardiogram signal to an external terminal. The analysis condition processing unit 142 may control an external terminal to display the electrocardiogram output data. The analysis condition processing unit 142 may control the analysis condition to be input using an analysis condition input interface included in the electrocardiogram output data. The analysis condition processing unit 142 may generate electrocardiogram output data for displaying past medical history, current questionnaires, and results of the questionnaire of a corresponding target object. Here, the questionnaire may be data including answers of a patient or a target object to questions provided by a medical staff. The questionnaire or the result of the questionnaire may include information related to pain in the heart. The analysis condition processing unit 142 may determine one or more labels related to past medical history, the questionnaires, etc. of a target object by using a table indicating the relationship between medical history and labels and retrieve sections of an electrocardiogram signal for labels related to past medical history, questionnaires, etc., thereby generating output data regarding the sections of the electrocardiogram signal. The table indicating the relationship between medical history and labels may be stored in the server 100 or stored in an external device and received through a network. The table indicating the relationship between medical history and labels may be changed by inputs of an electrocardiogram signal, medical history information of the target object, etc. The table indicating the relationship between medical history (type of disease, time of occurrence, etc.) and labels may be changed by an expert. Data regarding labels related to other life characteristic information and biometric information (age, gender, residence, occupation, race, smoking status, drinking status, etc.) of the target object may be generated and managed. Also, a medical staff may add additional labels (e.g., time at which a person subject to electrocardiogram measurement feels abnormal and symptoms thereof) from the person through a questionnaire. The analysis condition processing unit 142 may determine a label related to the target object based on such information and generate data regarding sections classified by the label.

The electrocardiogram output data may be displayed by arranging an electrocardiogram signal according to labels. For example, the electrocardiogram output data may display an electrocardiogram signal by dividing the electrocardiogram signal into sections classified by a first label, a second label, a third label, and so on. The electrocardiogram output data may be implemented to display sections corresponding to the first label, sections corresponding to the second label, and sections corresponding to the third label at once.

The electrocardiogram output data may include data arranged according to priorities of labels. The analysis condition processing unit 142 may determine priorities of labels based on information related to a target object and display section data corresponding to respective labels in an order according to the priorities. For example, the analysis condition processing unit 142 may set priorities for sections according to past medical history, current questionnaire results, drinking status, smoking status, gender, age, and the like. The priority may be set for each label, but is not limited thereto. The analysis condition processing unit 142 may generate section data in which a section having a high priority is arranged in a priority order. The priorities may be used in the process of estimating an analysis time.

The medical staff terminal 21 may access the electrocardiogram data processing server 100, receive electrocardiogram output data including an electrocardiogram signal and classification data regarding the electrocardiogram signal, and input analysis conditions regarding the classification data regarding the electrocardiogram signal. The analysis conditions may be set to a set of one or more labels, time, a disease, a symptom, etc. The analysis conditions may be set to a first label and a second label. The analysis condition processing unit 142 may separately search for and provide sections including pre-set analysis conditions. The analysis condition processing unit may generate location information of sections of the first and second labels, and generate signal sections of the first and second labels as data based on the locations. The analysis condition processing unit 142 may generate data regarding signal sections corresponding to analysis conditions according to the analysis conditions set to a label set and time. When the analysis condition is a disease, the analysis condition processing unit 142 may determine a label related to the disease and convert the label into an analysis condition.

The analysis condition processing unit 142 may classify an electrocardiogram signal by a certain time unit, e.g., daily or weekly, according to the analysis condition and generate data corresponding to a daily analysis condition. The analysis condition processing unit 142 may transmit data corresponding to the daily analysis condition to an external terminal in this regard. The external terminal may process the data corresponding to the daily analysis condition to be displayed. Since the rhythm of the human body has a cycle of 24 hours per day, it is preferable that a measured electrocardiogram signal is also displayed in the unit of 24 hours or one day. Also, questionnaire data regarding a target object may be generated in the unit of one day. The target object may also remember symptoms, pain, etc. in the cycle of one day, that is, 24 hours.

The analysis condition processing unit 142 may extract period information regarding an analysis condition from an electrocardiogram signal. The expected analysis time calculation unit 143 may calculate an expected analysis time in consideration of period information regarding sections corresponding to analysis conditions and analysis time of the sections corresponding to the respective analysis conditions. The expected analysis time calculation unit 143 may calculate an expected analysis time by multiplying a section occurring period by the analysis time of the sections. The expected analysis time calculation unit 143 may determine an occurrence pattern of sections corresponding to analysis conditions and calculate an expected analysis time according to the occurrence pattern. The expected analysis time may be calculated as a range between the minimum time and the maximum time. The expected analysis time calculation unit 143 may calculate analysis times of sections corresponding to analysis conditions by using machine-learned data, an algorithm, etc. Also, the expected analysis time calculation unit 143 may calculate analysis time of sections corresponding to analysis conditions based on the history of analyses performed by a corresponding analyst. The expected analysis time calculation unit 143 may calculate analysis time of sections corresponding to analysis conditions based on the history of analyses performed by other analysts.

The expected analysis time calculation unit 143 may calculate a noise duration from among parameters used for estimating analysis time, determine the ratio of the noise duration, and calculate an expected analysis time. Here, the noise is generated while measuring an electrocardiogram signal and included in the electrocardiogram signal, and may be generated by the movement of a target object, voltages from other muscles generated due to the movement of the target object, etc. Also, the noise may be generated by static electricity and the collision of electrical signals inside an electrocardiogram measuring device. The noise may be generated by a change in a connection relationship between an electrocardiogram measuring device and a target object. For example, a change in a voltage value due to factors other than the movement of the heart may correspond to the noise. Since the noise included in an electrocardiogram signal may affect the analysis time for the electrocardiogram signal, it is necessary to search for information regarding the noise to calculate an expected analysis time. The expected analysis time calculation unit 143 may transmit data regarding a calculated expected analysis time to an external terminal.

The expected analysis time calculation unit 143 may calculate an expected analysis time based on an analysis of a noise occurrence pattern. The noise occurrence pattern may follow a rule between noise occurring time points.

The expected analysis time calculation unit 143 may extract noise durations from analysis data regarding an electrocardiogram signal and determine whether a ratio of extracted noise duration is greater than or less than a pre-set reference ratio. The expected analysis time calculation unit 143 may calculate noise durations and a ratio of the noise durations for all or a portion of the electrocardiogram signal. A signal to be analyzed may include signal sections classified as analysis conditions. The reference ratio may be set by an accessing medical staff.

The expected analysis time calculation unit 143 may transmit data regarding calculated noise durations and a ratio of the noise durations to an external terminal. Data regarding noise may be processed to be displayed in an external terminal. The external terminal may input a modified input for the data regarding noise durations, and the expected analysis time calculation unit 143 may receive such a modified input and perform a process corresponding to the modified input.

When the modified input is an input for correcting an analysis condition or an analysis section, the expected analysis time calculation unit 143 may obtain a signal to be analyzed in correspondence to the analysis condition or the analysis section again in response to the modified input and re-calculate noise durations and a ratio of the noise duration with respect to the signal to be analyzed.

When the modified input is an input for correcting a target time, the expected analysis time calculation unit 143 may generate a result data of changing the target time in response to the modified input. An analysis request signal for the electrocardiogram signal may be generated based on a changed target time.

The medical staff terminal 21 may input a modified input for an analysis condition through a questionnaire with a target object. During the questionnaire with the target object, symptom (discomfort) detection information like a time at which symptoms (discomfort) occurred and a detected time section of the symptom (discomfort) may be checked and the analysis condition may be changed to analyze the times.

Here, the symptom (discomfort) detection information may be obtained by a medical staff from a patient through a questionnaire or may be generated by an input made by the patient while an electrocardiogram signal is being measured. The symptom detection information may be generated through measured biometric information. Here, the measured biometric information may include a respiration/heart rate value, a motion value, a sound value, a blood pressure value, a blood sugar value, an amount of food intake, an exercise amount, a stress index, a sleep time/quality, etc. When the symptom (discomfort) detection information is input or generated based on biometric information while an electrocardiogram signal is being measured, the electrocardiogram signal may include the symptom (discomfort) detection information. Also, in a situation in which an urgent analysis is needed, an analysis time needed for the analysis of an electrocardiogram signal with respect to only a designated period may be calculated.

Analysis conditions may be set by combining various conditions. For example, cases in which cardiac arrest may be predicted, e.g., a case in which ventricular fibrillation or atrial block is present at a heart rate below a certain level or a case in which ventricular tachycardia is present at a high heart rate may be set as analysis conditions. The analysis conditions may be converted into corresponding sections included in an electrocardiogram signal. The expected analysis time calculation unit 143 may calculate an expected analysis time of an electrocardiogram signal based on a noise pattern of the electrocardiogram signal. The expected analysis time calculation unit 143 may extract noise sections included in the electrocardiogram signal, calculate an analysis time for the noise sections based on signal lengths of the noise sections, and calculate an expected analysis time based on the analysis time for the noise sections. The expected analysis time calculation unit 143 may select data of interest of the electrocardiogram signal corresponding to a section of interest and calculate an expected analysis time for the data of interest. A first date determined by a certain condition in a measurement period may be determined as a section of interest. The expected analysis time calculation unit 143 may calculate an expected analysis time based on an occurrence pattern of sections corresponding to the analysis condition for the electrocardiogram signal. The expected analysis time calculation unit 143 may calculate an expected analysis time in consideration of a noise pattern and an occurrence pattern in sections corresponding to the analysis condition. The expected analysis time calculation unit 143 may calculate an analysis time regarding noise by using machine learned data. Also, the expected analysis time calculation unit 143 may calculate analysis time regarding noise based on the history of analyses performed by a corresponding analyst. The expected analysis time calculation unit 143 may calculate analysis time regarding noise based on the history of analyses performed by other analysts.

Figure 4:
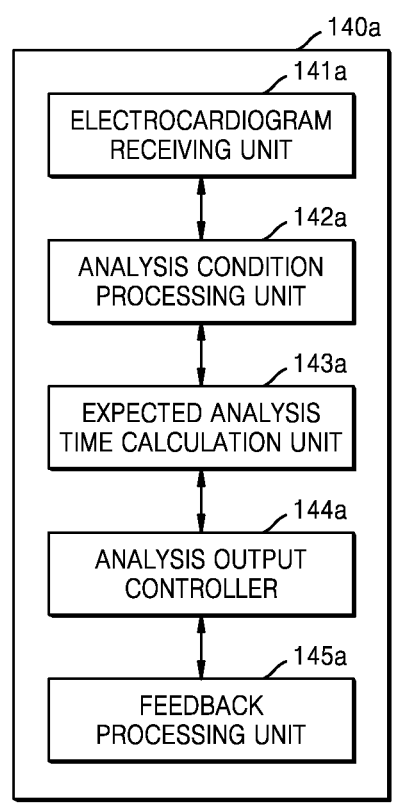
FIG. 4 is a block diagram of an electrocardiogram signal analysis unit that generates an electrocardiogram analysis request by using feedback from an analyst terminal according to one or more embodiments.

FIG. 4 is a block diagram of an electrocardiogram signal analysis unit 140a that generates an electrocardiogram analysis request by using feedback from an analyst terminal according to one or more embodiments.

The electrocardiogram signal analysis unit 140a may be a component that may be replaced by the electrocardiogram signal analysis unit 140.

The electrocardiogram signal analysis unit 140a may include an electrocardiogram receiving unit 141a, an analysis condition processing unit 142a, an expected analysis time calculation unit 143a, and a feedback processing unit 145a.

The electrocardiogram receiving unit 141a may receive data regarding an electrocardiogram signal. The data regarding an electrocardiogram signal may include an electrocardiogram signal and classification data regarding the electrocardiogram signal. The data regarding the electrocardiogram signal may be data regarding an electrocardiogram signal measured for a certain period, e.g., one week or 14 days. Classification data regarding an electrocardiogram signal may include category values corresponding to respective signal waveforms of the electrocardiogram signal while displaying the signal waveforms in time series. The category values may be values converted into labels. The category values may include, but are not limited to, RR Pause, Bradycardia, NN delay, Heart Block, Atrial Fibrillation (AF), SVE, SVE tachycardia, R on T, VE tachycardia, VE run, PVC, Triplet (PVC), Couplet (PVC), Bigeminy (PVC) .), Ventricular Escape, etc. The category values may be converted into corresponding labels and included in classification data regarding the electrocardiogram signal.

In another embodiment, the electrocardiogram receiving unit 141a may analyze signal waveforms of an electrocardiogram signal and generate classification data regarding the electrocardiogram signal. The electrocardiogram receiving unit 141a may generate classification data regarding the electrocardiogram signal by dividing the electrocardiogram signal into signal segments according to signal waveforms and classifying the electrocardiogram signal by setting each signal segment to one of category values, thereby generating the classification data regarding the electrocardiogram signal.

The analysis condition processing unit 142a may transmit an electrocardiogram signal and classification data regarding the electrocardiogram signal to an external terminal, control the external terminal to input analysis conditions for the electrocardiogram signal, and receive data regarding the analysis conditions. The analysis conditions may include information such as labels, times, diseases, etc.

When the data regarding the analysis conditions is received, the analysis condition processing unit 142a may separately search for and provide sections including pre-set analysis conditions. The analysis condition processing unit 142a may generate data regarding positions of sections including the first label and the second label and the sections. The analysis condition processing unit 142a may generate data regarding signal sections corresponding to analysis conditions according to the analysis conditions set to a label set and time. When the analysis condition is a disease, the analysis condition processing unit 142a may determine a label related to the disease and convert the label into an analysis condition. The analysis condition processing unit 142a may cause an analysis condition to be input from an external terminal. The analysis condition processing unit 142a may determine labels, analysis sections, etc. related to a target object according to the analysis conditions obtained from an analysis output controller 144a and generate data regarding sections classified according to labels and analysis sections.

The analysis condition processing unit 142a may classify an electrocardiogram signal by a certain time unit, e.g., daily or weekly, according to the analysis condition and generate data corresponding to a daily analysis condition. The analysis condition processing unit 142a may transmit data corresponding to the daily analysis condition to an external terminal in this regard. The external terminal may process the data corresponding to the daily analysis condition to be displayed.

The analysis condition processing unit 142a may extract period information regarding an analysis condition from an electrocardiogram signal. The expected analysis time calculation unit 143a may calculate an expected analysis time in consideration of period information regarding sections corresponding to analysis conditions and analysis time of the sections corresponding to the respective analysis conditions. The expected analysis time calculation unit 143a may calculate an expected analysis time by multiplying a section occurring period by the analysis time of the sections. The expected analysis time calculation unit 143a may determine an occurrence pattern of sections corresponding to analysis conditions and calculate an expected analysis time according to the occurrence pattern. The expected analysis time may be set as a range between the minimum time and the maximum time.

The expected analysis time calculation unit 143a may preferentially use a noise duration from among parameters used to predict an analysis time. This noise duration may be excluded from analysis or used in conjunction with other biometric signals (e.g., a movement).

The expected analysis time calculation unit 143a may calculate an expected analysis time based on an analysis of a noise occurrence pattern. The noise occurrence pattern may follow a rule between noise occurring time points. The noise occurrence pattern may vary depending on a noise source. When noise occurs due to degradation of the quality of adherence of an electrocardiogram measuring electrode on the skin, the noise may be excluded from analysis of an electrocardiogram signal. However, arrhythmias may be determined by using a heart rate obtained from an electrocardiogram signal according to whether noise occurs due to a movement of a target object (e.g., a signal generated from a muscle during sleep or an exercise).

The expected analysis time calculation unit 143a may extract noise durations from analysis data regarding an electrocardiogram signal and determine whether a ratio of extracted noise duration is greater than or less than a pre-set reference ratio. The expected analysis time calculation unit 143a may calculate noise durations and a ratio of the noise durations for all or a portion of the electrocardiogram signal. A signal to be analyzed may include signal sections classified as analysis conditions. The reference ratio may be set by an accessing medical staff.

The expected analysis time calculation unit 143a may transmit data regarding calculated noise durations and a ratio of the noise durations to an external terminal. Data regarding noise may be processed to be displayed in an external terminal. The external terminal may input a modified input for the data regarding noise durations, and the expected analysis time calculation unit 143a may receive such a modified input and perform a process corresponding to the modified input.

When the modified input is an input for correcting an analysis condition or an analysis section, the expected analysis time calculation unit 143 may obtain a signal to be analyzed in correspondence to the analysis condition or the analysis section again in response to the modified input and re-calculate noise durations and a ratio of the noise duration with respect to the signal to be analyzed. In this process, various analysis conditions may be set depending on the cause of the noise.

When the modified input is an input for correcting a target time, the expected analysis time calculation unit 143a may generate a result data of changing the target time in response to the modified input. An analysis request signal for the electrocardiogram signal may be generated based on a changed target time.

The medical staff terminal 21 may input a modified input for an analysis condition through a questionnaire with a target object. During the questionnaire with the target object, symptom (discomfort) detection information like a time at which symptoms (discomfort) occurred and a detected time section of the symptom (discomfort) may be checked and the analysis condition may be changed to analyze the times. Here, the symptom (discomfort) detection information may be obtained by a medical staff from a patient or may be generated by an input made by the patient while an electrocardiogram signal is being measured. When the symptom (discomfort) detection information is generated while an electrocardiogram signal is being measured, the electrocardiogram signal may include the symptom (discomfort) detection information. It is obvious that the past electrocardiogram analysis information and/or other medical history of a patient may be referred to during a questionnaire process.

The analysis output controller 144a may generate electrocardiogram output data for displaying the electrocardiogram signal and the classification data regarding the electrocardiogram signal and transmit the electrocardiogram output data to an external terminal.

Before analysis conditions are input, the analysis output controller 144a may control, such that analysis conditions are input based on an analysis condition input interface included in the electrocardiogram output data. The analysis output controller 144a may generate electrocardiogram output data for displaying past data regarding a corresponding target object, such as past medical history, a current questionnaire, results of the questionnaire, and abnormality with respect to electrocardiogram signals measured in the past. The analysis output controller 144a may determine one or more labels related to the past medical history and/or the questionnaires of a target object by using a table indicating the relationship between medical history and labels and generate electrocardiogram output data for including one or more labels related to the past medical history and/or the questionnaires.

Also, the analysis output controller 144a may generate output data regarding sections of an electrocardiogram signal to be displayed by searching for sections of an electrocardiogram signal corresponding to labels related to the past medical history and/or the questionnaires.

In the present specification, a table indicating the relationship between the past medical history and/or the questionnaires and labels may be stored in the server 100 or stored in an external device and received through a network. The table indicating the relationship between the past medical history and/or the questionnaires and labels may be changed by inputs of an electrocardiogram signal, the medical history information of the target object, and questionnaires (current or past). The table indicating the relationship between medical history (type of disease, time of occurrence, etc.) and/or the questionnaires (current or past) and labels may be changed by an expert. Data regarding labels related to age, gender, residence, occupation, race, smoking status, drinking status, etc. of the target object may be generated and managed.

The electrocardiogram output data may be displayed by arranging an electrocardiogram signal according to labels. For example, the electrocardiogram output data may display an electrocardiogram signal by dividing the electrocardiogram signal into sections classified by a first label, a second label, a third label, and so on. The electrocardiogram output data may be implemented to display sections corresponding to the first label, sections corresponding to the second label, and sections corresponding to the third label at once.

The electrocardiogram output data may include data arranged according to priorities of labels. The analysis output controller 144a may determine priorities of labels based on information related to a target object and display section data corresponding to respective labels in an order according to the priorities. For example, the analysis output controller 144a may generate labels that need to be analyzed in detail according to the past medical history, current questionnaire results, drinking status, smoking status, gender, age, etc. of a target object and generate output data provided to sections corresponding to the respective labels. Also, the analysis output controller 144a may set priorities for labels or signal sections according to the past medical history, questionnaires, drinking status, smoking status, gender, age, etc. of a target object, determine labels corresponding to the priorities, and generate section data corresponding to the respective labels based on the labels. For example, when a first user has a history that an 'abnormal signal' occurs after 'bradycardia', output data separately providing labels and/or sections related to the 'bradycardia' may be generated. Based on symptom (discomfort) detection information regarding a second user, output data providing signal sections corresponding to the symptom (discomfort) detection information and labels of the corresponding signal sections may be generated. The analysis output controller 144a may generate output data that is displayed at once for labels classified according to symptoms and signal sections corresponding to the labels. The analysis output controller 144a may generate output data for displaying labels classified according to symptoms and signal sections corresponding to the labels at once regardless of time. The analysis output controller 144a may generate output data in which an electrocardiogram signal is filtered with respect to a duration, an occurrence cycle, an occurring time section, etc. For example, the analysis output controller 144a may generate output data for displaying signal sections regarding labels lasting for 30 seconds or longer. However, one or more embodiments are not limited thereto, and signal sections regarding labels having a duration input by a user may be filtered. The analysis output controller 144a may generate output data for displaying signal sections regarding labels that occurred 10 times or more frequently during one day. However, one or more embodiments are not limited thereto, and signal sections regarding labels having an occurring frequency input by a user may be filtered. Also, output data may be displayed in the unit of a day (24 hours) or analyzed and displayed in a specific time band.

The medical staff terminal 21 may access the electrocardiogram data processing server 100, receive electrocardiogram output data including an electrocardiogram signal and classification data regarding the electrocardiogram signal, and input analysis conditions regarding the classification data regarding the electrocardiogram signal. The analysis conditions may be set to a set of one or more labels, time, a disease, a disease, etc. The analysis condition may be set to, for example, a first label and a second label, including one or more labels.

The feedback processing unit 145a may generate output data regarding a screen image for analyzing an electrocardiogram signal in response to an analysis request signal. The feedback processing unit 145a may transmit such output data to a designated analyst terminal.

The output data regarding the screen image for analyzing an electrocardiogram signal may include analysis target sections set for the electrocardiogram signal and comments input for sections to be analyzed. Also, the output data regarding the screen image for analyzing an electrocardiogram signal may include a transmission-related region for sending comments and inquiries to a medical staff.

The feedback processing unit 145a may transmit an input comment of an analyst to a medical staff terminal and transmit a reply message thereto to a terminal of the analyst. The feedback processing unit 145a may transmit a comment of a medical staff to an analyst terminal. The comment of the analyst and the comment of the medical staff may be stored in association with a corresponding electrocardiogram signal.

The feedback processing unit 145a may generate data re-generated with various options with respect to an electrocardiogram signal and classification data regarding the electrocardiogram signal and transmit an analysis request signal regarding the data. The feedback processing unit 145a may generate data by excluding abnormal signal sections of a signal according to an option of excluding abnormal signal durations and transmit an analysis request signal regarding the data. The feedback processing unit 145a may generate data regarding signal sections corresponding to labels with high weights according to an option of assigning a weight to each label and transmit an analysis request signal regarding the data.

The feedback processing unit 145a may generate signal sections corresponding to an analysis condition or signal sections corresponding to an option as data and transmit an analysis request signal regarding the data to an analyst terminal. Here, the analyst terminal may be determined by a medical staff terminal, by a request from the analyst terminal, or by a task-assigning algorithm.

The feedback processing unit 145a may recommend an analyst terminal suitable for an analysis request signal. The feedback processing unit 145a may determine a suitable analyst terminal in consideration of signal sections, labels, a past medical history of a corresponding target object, and questionnaires included in an analysis request signal. A suitable analyst terminal may be determined based on the history of analyses performed by one or more analysts in the past. The feedback processing unit 145a may determine an analyst having the history of analyses for labels of signal sections and an analyst having the history of analyses for signal sections corresponding to the past medical history and/or the questionnaire of a target object as a suitable analyst.

The feedback processing unit 145a may receive an analysis report corresponding to an analysis request signal. The feedback processing unit 145a may perform a function of transmitting a reminder for an analysis report. When an analysis report is received, the feedback processing unit 145a may transmit a notification thereof to a medical staff terminal.

The electrocardiogram data processing server 100 may store and manage an electrocardiogram signal, classification data regarding the electrocardiogram signal, analysis conditions input for the electrocardiogram signal, an expected analysis time regarding the electrocardiogram signal, an analysis report regarding the electrocardiogram signal, feedback data additionally input for the electrocardiogram signal, etc. The electrocardiogram data processing server 100 may manage stored data through an internal medium or an external electronic device.

Figure 5:
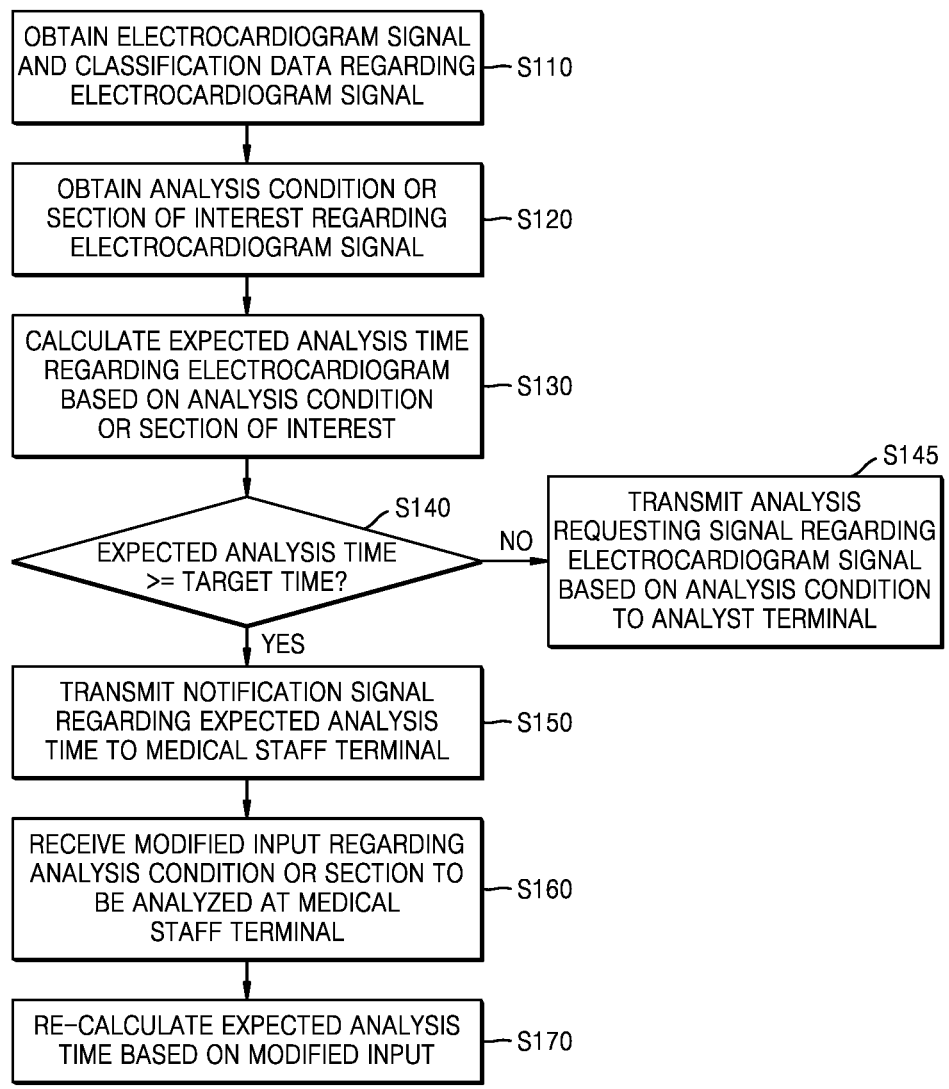
FIG. 5 is a flowchart of a method of processing electrocardiogram data according to one or more embodiments.

FIG. 5 is a flowchart of a method of processing electrocardiogram data according to one or more embodiments.

In operation S110, the electrocardiogram data processing server 100 may obtain an electrocardiogram signal and classification data regarding the electrocardiogram signal. The electrocardiogram signal may be measured for a certain period, for e.g., 2 days or 14 days. Classification data regarding an electrocardiogram signal may include category values corresponding to respective signal waveforms of the electrocardiogram signal while displaying the signal waveforms in time series. The category values may be values converted into labels. The electrocardiogram data processing server 100 may generate classification data regarding the electrocardiogram signal by dividing the electrocardiogram signal into signal segments according to signal waveforms and setting each signal segment to one of category values, thereby generating the classification data regarding the electrocardiogram signal. It is important to note that a classification algorithm is not 100% perfect. So, analyst should involve to confirm and correct the machine-decision classifications. However, this correction process will be replaced by artificial intelligence.

In operation S120, the electrocardiogram data processing server 100 may obtain an analysis condition or a section of interest regarding the electrocardiogram signal. The analysis condition may be determined by the medical staff terminal. The electrocardiogram data processing server 100 may transmit the electrocardiogram signal and electrocardiogram output data for displaying classification data regarding the electrocardiogram signal to a medical staff terminal. The medical staff terminal may control to input analysis conditions for displayed electrocardiogram output data. The analysis conditions may include label values or time values. In this case, in the case of a first iteration, a default value or a past setting value for a patient may be used as an analysis condition. Also, a set value recommended by artificial intelligence may be used as an analysis condition. Such analysis conditions may be set by a medical staff in advance or may be interactively performed by the medical staff. In operation S120, an analysis condition for designating the entire section of the electrocardiogram signal may be obtained.

A section of interest may be determined by using classification data regarding an electrocardiogram signal, may be determined by using the electrocardiogram signal and detection information included in additionally input biometric information, or may be determined by using the past medical history and/or the questionnaires of a target object. The section of interest may be determined based on analysis conditions. The additionally input biometric information may be related to biometric information measured along with the electrocardiogram signal. The biometric information may include a body temperature value, a blood sugar value, a blood pressure value, and a respiration value.

In operation S130, the electrocardiogram data processing server 100 may calculate an expected analysis time for the electrocardiogram signal based on analysis conditions. The electrocardiogram data processing server 100 may calculate an analysis time for each section of the electrocardiogram signal. The electrocardiogram data processing server 100 may calculate an expected analysis time for the electrocardiogram signal based on the analysis times of respective sections. The electrocardiogram data processing server 100 may extract sections corresponding to analysis conditions and calculate an expected analysis time regarding the sections. The electrocardiogram data processing server 100 may calculate the expected analysis time in consideration of the occurrence pattern of the sections, analysis times for the sections, a noise generation pattern in the sections, etc.

In S140, when it is detected that the expected analysis time is equal to or greater than a pre-set target time, the electrocardiogram data processing server 100 may transmit a notification signal regarding the expected analysis time to the medical staff terminal (operation S150). The electrocardiogram data processing server 100 may transmit an analysis request signal based on an analysis condition for the electrocardiogram signal to an analyst terminal when the expected analysis time is less than the pre-set target time (operation S145). When the expected analysis time is less than the pre-set target time, the electrocardiogram data processing server 100 may transmit a notification signal regarding the expected analysis time to the medical staff terminal.

In operation S160, the electrocardiogram data processing server 100 may receive a modified input regarding an analysis condition or an analysis section from the medical staff terminal.

In operation S170, the electrocardiogram data processing server 100 may re-calculate an expected analysis time based on the modified input. When the modified input is an input for correcting an analysis condition or an analysis section, the electrocardiogram data processing server 100 may obtain a signal to be analyzed in correspondence to the analysis condition or the analysis section again in response to the modified input and re-calculate noise durations and a ratio of the noise duration with respect to the signal to be analyzed.

When the modified input is an input for correcting a target time, the electrocardiogram data processing server 100 may generate a result data of changing the target time in response to the modified input. An analysis request signal for the electrocardiogram signal may be generated based on a changed target time.

Figure 6:
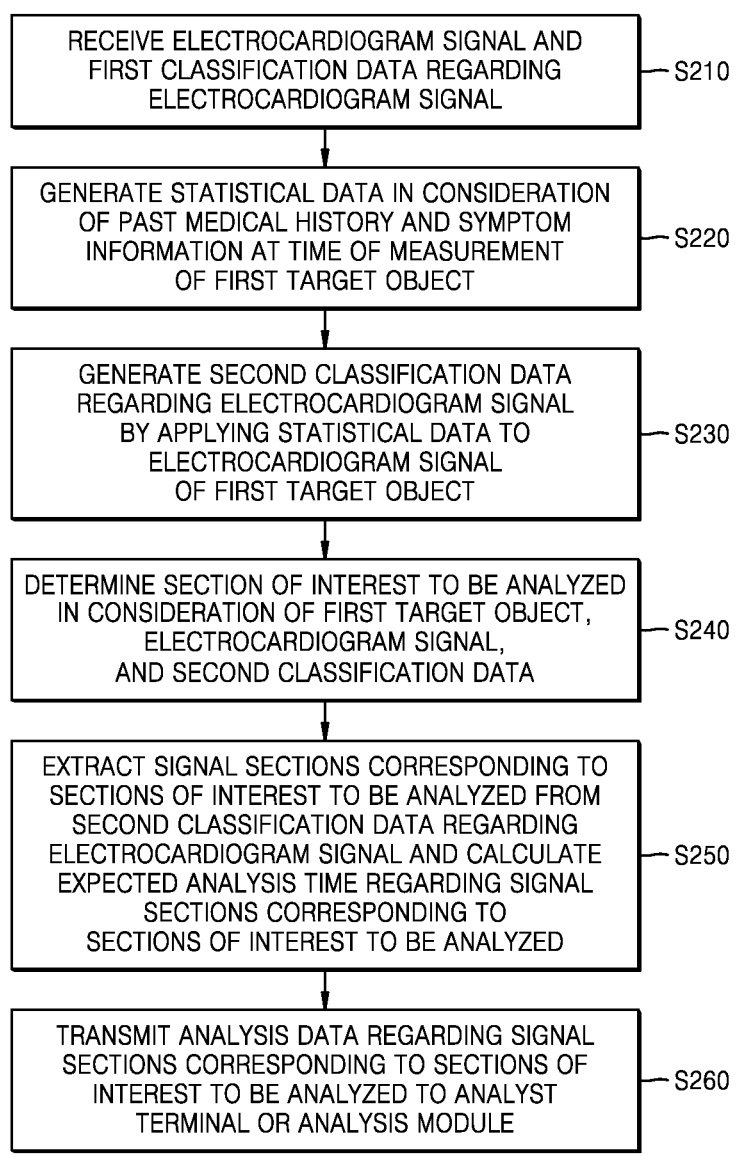
FIG. 6 is a flowchart of a method of generating and processing analysis data regarding an electrocardiogram signal according to one or more embodiments.

FIG. 6 is a flowchart of a method of generating and processing analysis data regarding an electrocardiogram signal according to one or more embodiments.

In operation S210, the electrocardiogram data processing server 100 may receive an electrocardiogram signal and first classification data regarding the electrocardiogram signal.

In operation S220, the electrocardiogram data processing server 100 may generate statistical data in consideration of the past medical history of a target object and symptom information at the time of measurement. The electrocardiogram data processing server 100 may calculate statistical data regarding the target object based on an electrocardiogram signal measured for the target object (a user or a patient) and analysis data regarding the electrocardiogram signal. The statistical data may include pattern information regarding the electrocardiogram signal when the target object feels pain, frequencies of patterns occurring in the electrocardiogram signal, occurrence periods of the patterns, data regarding the patterns per certain unit period of the electrocardiogram signal, and pattern information regarding the electrocardiogram signal when a danger occurs in a biometric signal of the target object. The symptom information at the time of measurement may include data input by the target object, questionnaire data, signals related to diseases of the target object, and signals occurring in groups of diseases of the target object.

In operation S230, the electrocardiogram data processing server 100 may generate a second classification data regarding the electrocardiogram signal by applying the statistical data to the electrocardiogram signal of the target object. The second classification data is generated by using pain information input by the target object and statistical data based on diseases of the target object and groups of the diseases, and, in detail, may further include label information, category information, comment information, etc. regarding measured electrocardiogram signal sections.

In operation S240, the electrocardiogram data processing server 100 may determine a section of interest to be analyzed in consideration of the target object, the electrocardiogram signal, and the second classification data.

In operation S250, the electrocardiogram data processing server 100 may extract signal sections corresponding to the section of interest to be analyzed from the second classification data regarding the electrocardiogram signal and calculate an expected analysis time for the signal sections corresponding to the section of interest to be analyzed.

When it is determined that a calculated expected analysis time is equal to or greater than a pre-set reference value, the electrocardiogram data processing server 100 may perform operations of generating the second classification data and determining the section of interest to be analyzed again. When the calculated expected analysis time is equal to or greater than the pre-set reference value, the electrocardiogram data processing server 100 may perform operations of generating the second classification data and determining the section of interest to be analyzed according to the second classification data again to reduce the expected analysis time. In this case, the electrocardiogram data processing server 100 may change a priority value for generating the second classification data. Each of the first classification data and the second classification data may further include a priority value, and the electrocardiogram data processing server 100 may re-generate classification data including label information and category information according to priority values.

In operation S260, the electrocardiogram data processing server 100 may transmit analysis data regarding the signal sections corresponding to the section of interest to be analyzed to the analyst terminal or an analysis module.

Therefore, the electrocardiogram data processing server 100 may generate classification data using statistical information like past medical history information (diseases, etc.), pain information, and questionnaire information regarding the target object. The electrocardiogram data processing server 100 may determine a section of interest to be analyzed by using past medical history information, pain information, questionnaire information, etc. regarding a target object. The electrocardiogram data processing server 100 may calculate a section of interest to be analyzed and an analysis time needed to analyze the section of interest to be analyzed by utilizing the past medical history, the pain information, the questionnaire information, etc. of a target object.

Figure 7:
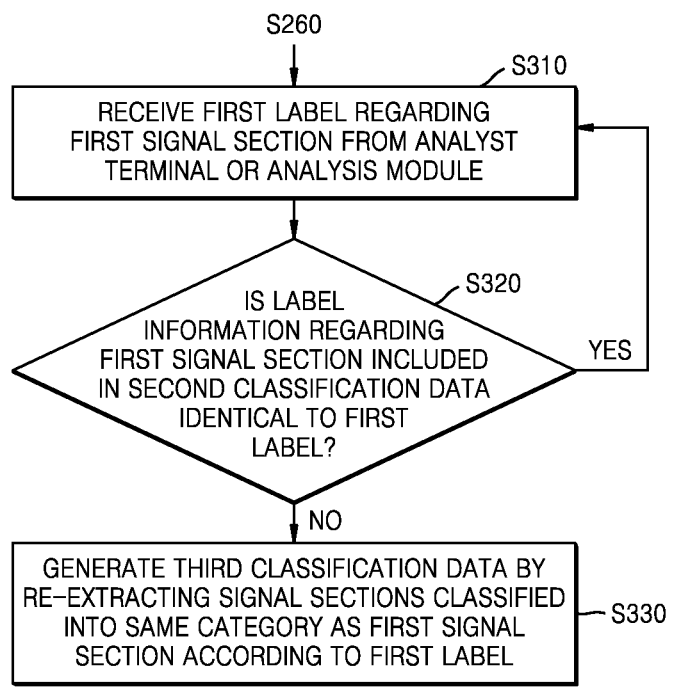
FIG. 7 is a flowchart of a method of comparing a label generated according to one or more embodiments with a label input by an analyst terminal or an analysis module.

FIG. 7 is a flowchart of a method of comparing a label generated according to one or more embodiments with a label input by an analyst terminal or an analysis module.

In operation S310, the electrocardiogram data processing server 100 may receive a first label for a first signal section from the analyst terminal or the analysis module.

In operation S320, the electrocardiogram data processing server 100 may compare label information regarding the first signal section included in the second classification data with the first label and determine whether they are the same.

In operation S330, when the label information regarding the first signal section is different from the first label, the electrocardiogram data processing server 100 may re-extract signal sections classified into the same category (or label) as the first signal section. The electrocardiogram data processing server 100 may generate third classification data by re-classifying signal sections to the first label.

Therefore, a label regarding the first signal section automatically generated by the electrocardiogram data processing server 100 may be compared with a label input through the analyst terminal or a separate analysis module, thereby changing the label regarding the first signal section to a newly input label. In other words, when the analyst terminal or the analysis module determines that an automatically generated label is incorrect, the label information regarding a corresponding signal section may be changed, and label information regarding signal sections identical to the corresponding signal section may be changed overall.

Figure 8:
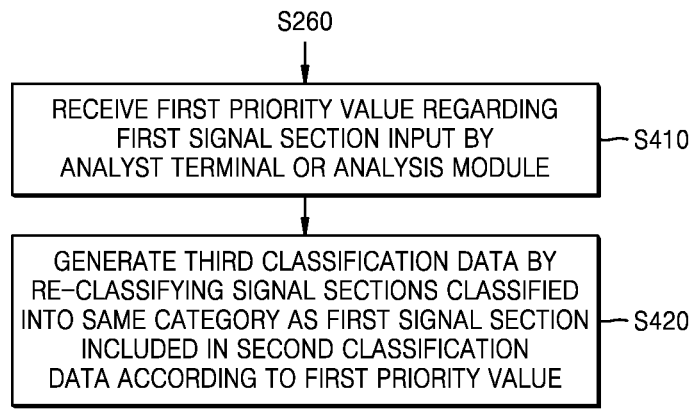
FIG. 8 is a flowchart of a method of comparing a priority value of a signal section generated according to one or more embodiments with a priority value input by an analyst terminal or an analysis module.

FIG. 8 is a flowchart of a method of comparing a priority value of a signal section generated according to one or more embodiments with a priority value input by an analyst terminal or an analysis module.

In operation S410, the electrocardiogram data processing server 100 may receive a first priority value for a first signal section input by an analyst terminal or an analysis module.

In operation S420, the electrocardiogram data processing server 100 may generate third classification data by re-classifying signal sections, which are included in the second classification data and are classified into the same category as the first signal section, by setting the first priority value to the signal sections.

Therefore, the electrocardiogram data processing server 100 may collectively change priority values for signal sections. The priority value may indicate importance in analyzing a disease or health status of a patient. The priority value may be set as a relative number. The electrocardiogram data processing server 100 may re-generate classification data according to a changed priority value.

Figure 9:
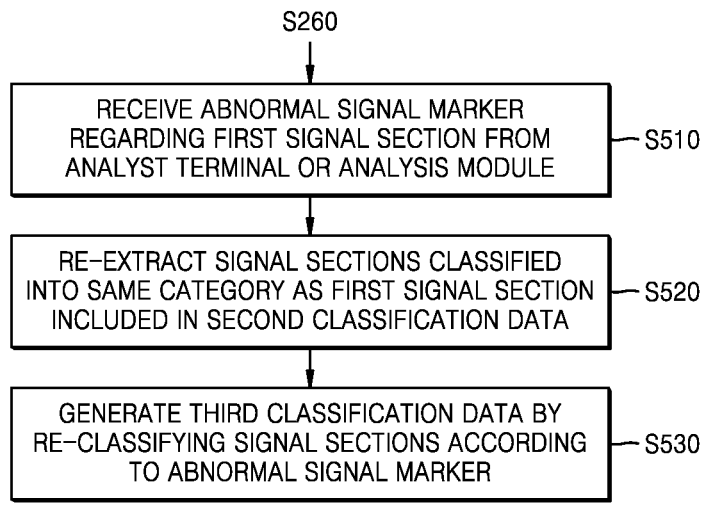
FIG. 9 is a flowchart of a method of comparing an abnormal signal marker label generated according to one or more embodiments with an abnormal signal marker input by an analyst terminal or an analysis module.

FIG. 9 is a flowchart of a method of comparing an abnormal signal marker label generated according to one or more embodiments with an abnormal signal marker input by an analyst terminal or an analysis module.

In operation S510, the electrocardiogram data processing server 100 may receive an abnormal signal marker for a first signal section input by an analyst terminal or an analysis module.

In operation S520, the electrocardiogram data processing server 100 may re-extract signal sections, which are included in the second classification data and classified into the same category (or label) as the first signal section.

In operation S530, the electrocardiogram data processing server 100 may generate third classification data by re-classifying signal sections according to the abnormal signal marker.

Therefore, the electrocardiogram data processing server 100 may re-generate classification data in consideration of an abnormal signal marker calculated by using another method. The electrocardiogram data processing server 100 may detect another signal section as an abnormal signal section according to the subjective viewpoint of an analyst or an analysis method of an analysis module.

Figure 10:
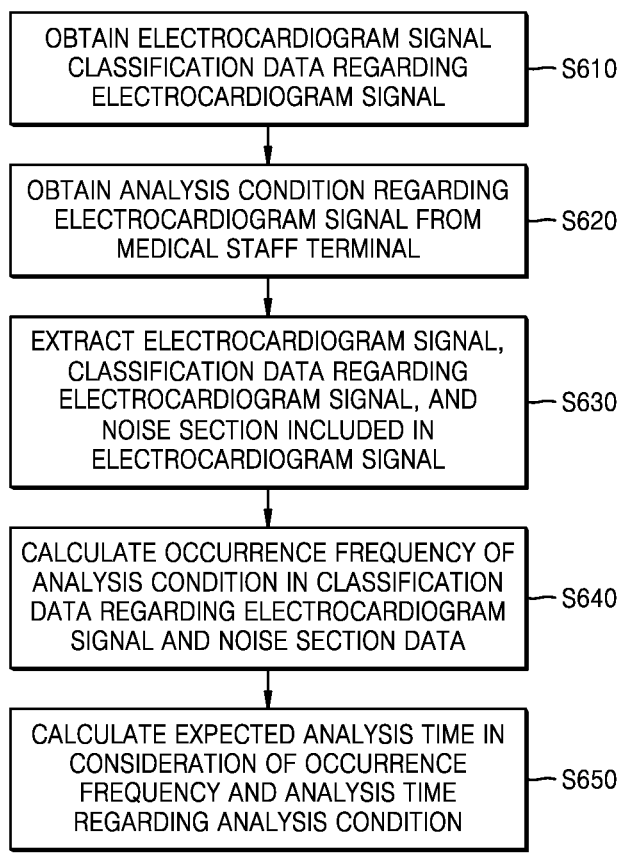
FIG. 10 is a flowchart of a method of calculating an expected analysis time according to one or more embodiments.

FIG. 10 is a flowchart of a method of calculating an expected analysis time according to one or more embodiments.

In operation S610, the electrocardiogram data processing server 100 may obtain an electrocardiogram signal and classification data regarding the electrocardiogram signal.

In operation S620, the electrocardiogram data processing server 100 may obtain an analysis condition regarding the electrocardiogram signal from a medical staff terminal.

In operation S630, the electrocardiogram data processing server 100 may extract an electrocardiogram signal, classification data regarding the electrocardiogram signal, and data regarding a noise section in a section corresponding to the analysis condition. The electrocardiogram data processing server 100 may separately calculate an analysis time for the noise section.

In operation S640, the electrocardiogram data processing server 100 may calculate the frequency of occurrence of the analysis condition from the classification data regarding the electrocardiogram signal. The electrocardiogram data processing server 100 may calculate the frequency of occurrence in consideration of time points at which sections corresponding to the analysis condition occur.

In operation S650, the electrocardiogram data processing server 100 may calculate an expected analysis time in consideration of the frequency of occurrence and the analysis time regarding the analysis conditions. The electrocardiogram data processing server 100 may calculate a first expected analysis time in consideration of the frequency of occurrence and the analysis time regarding a corresponding section in response to the analysis condition and calculate an expected analysis time by adding an analysis time for the noise section to the first expected analysis time. Here, for the expected analysis time, a standard time may be calculated based on the past performance of the analyst. Actual analysis time may vary according to analysts. An analyst may be selected by considering differences between analysts. Also, the electrocardiogram data processing server 100 may allow some or all of tasks of an analyst to be performed by an analysis module implemented with artificial intelligence.

FIG. 11 is a flowchart of a method of calculating an expected analysis time based on an analysis condition input as a label according to one or more embodiments.

In operation S710, the electrocardiogram data processing server 100 may obtain an electrocardiogram signal and classification data regarding the electrocardiogram signal.

In operation S720, the electrocardiogram data processing server 100 may generate output data for displaying classification data regarding the electrocardiogram signal.

In operation S730, the electrocardiogram data processing server 100 may transmit the output data to a medical staff terminal to display the electrocardiogram signal and the classification data regarding the electrocardiogram signal on the medical staff terminal. The output data may include information regarding total data of the electrocardiogram signal, a noise duration value, and a total monitoring time value and may include noise duration values for respective dates and monitoring time values for the respective dates. The electrocardiogram data processing server 100 may perform a process of analyzing an electrocardiogram signal according to an analysis condition and selecting a noise, thereby providing data analyzed according to the analysis condition and information regarding the noise including sections, occurring positions, and durations. Additionally, the output data may include information regarding whether a noise occurring rate is normal, high, or low.

In operation S740, the electrocardiogram data processing server 100 may receive an analysis condition including a first label and a second label selected by the medical staff terminal. The analysis condition may be determined from among labels regarding an electrocardiogram signal included in output data. However, the analysis condition is not limited thereto and may be selected from a list of labels included in the corresponding electrocardiogram signal.

In operation S750, when an analysis condition is received, the electrocardiogram data processing server 100 may calculate an expected analysis time based on the analysis condition and display the expected analysis time on the medical staff terminal. The electrocardiogram data processing server 100 may calculate a noise duration from among parameters used for prediction of an analysis time. The electrocardiogram data processing server 100 may calculate a noise occurring pattern based on the noise duration. The electrocardiogram data processing server 100 may calculate the occurrence patterns of sections corresponding to the first label and the second label regarding the electrocardiogram signal. The electrocardiogram data processing server 100 may calculate a first expected analysis time by multiplying analysis time for sections corresponding to the first label and the second label by the occurrence pattern of the corresponding section, calculate a second expected analysis time in consideration of the occurrence pattern of a noise in the electrocardiogram signal and an analysis time regarding the noise, and calculate a final expected analysis time by summing the first expected analysis time and the second expected analysis time.

Figure 12:
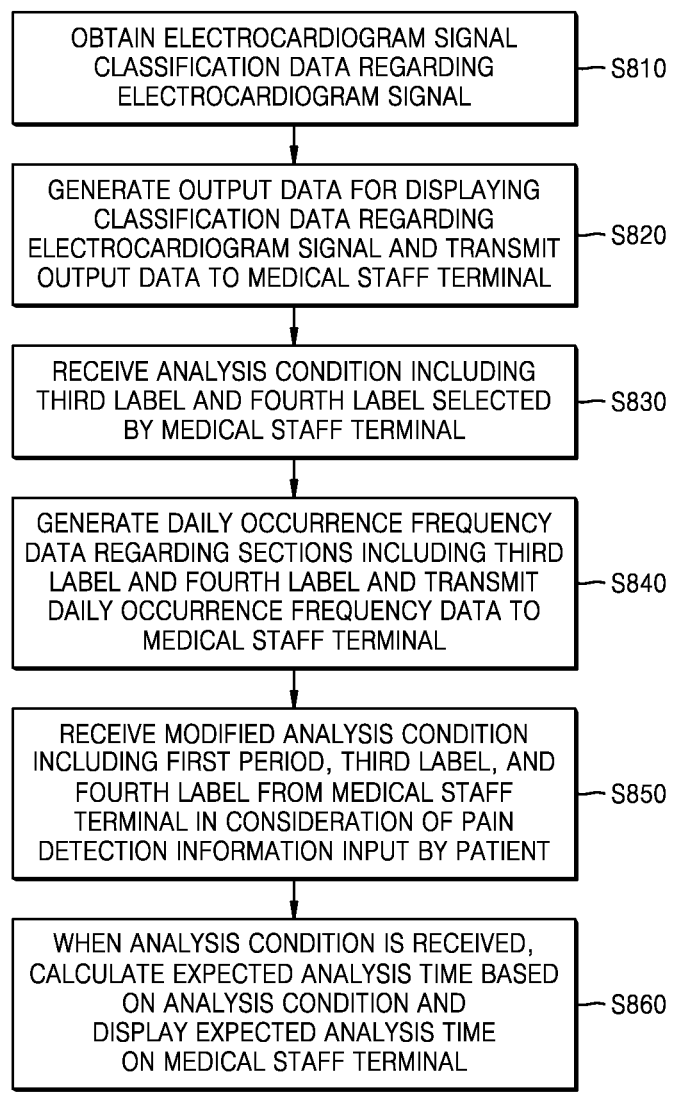
FIG. 12 is a flowchart of a method of re-generating and analyzing a changed condition according to symptom (discomfort) detection information according to one or more embodiments.

FIG. 12 is a flowchart of a method of re-generating and analyzing a changed condition according to symptom (discomfort) detection information according to one or more embodiments.

In operation S810, the electrocardiogram data processing server 100 may receive an electrocardiogram signal and classification data regarding the electrocardiogram signal.

In operation S820, the electrocardiogram data processing server 100 may generate output data for displaying classification data regarding the electrocardiogram signal and transmit the output data to a medical staff terminal.

In operation S830, the electrocardiogram data processing server 100 may receive an analysis condition including a third label and a fourth label selected by the medical staff terminal.

In operation S840, the electrocardiogram data processing server 100 may generate data regarding daily occurrence frequency of a section including the third label and the fourth label and transmit the data to the medical staff terminal.

In operation S850, the electrocardiogram data processing server 100 may receive a modified analysis condition including a first period, the third label, and the fourth label from the medical staff terminal in consideration of symptom (discomfort) detection information input by a patient. The symptom (discomfort) detection information is information input by the patient regarding a symptom (discomfort) felt during an electrocardiogram measurement and may include a time point at which the symptom (discomfort) is felt, a degree of the symptom (discomfort), details of the symptom (discomfort), etc. The symptom (discomfort) detection information may be included in the electrocardiogram signal or may be information obtained through separate communication with the patient (e.g., questionnaire, online treatment, etc.). The electrocardiogram data processing server 100 may modify an analysis condition based on the symptom (discomfort) detection information. Also, the symptom (discomfort) detection information may be checked and the analysis condition may be modified at the medical staff terminal. The electrocardiogram data processing server 100 may include a first period including a time point at which a symptom (discomfort) is detected in the analysis condition, such that the time point at which the symptom (discomfort) is detected may be analyzed in priority. The electrocardiogram data processing server 100 may receive an input for including the first period in an analysis condition from the medical staff terminal.

In operation S860, when an analysis condition is received, the electrocardiogram data processing server 100 may calculate an expected analysis time based on the analysis condition and display the expected analysis time on the medical staff terminal. The electrocardiogram data processing server 100 may extract sections including the third label and the fourth label from data regarding the first period, which is a modified changed analysis condition, and calculate an expected analysis time for the sections.

Figure 13:
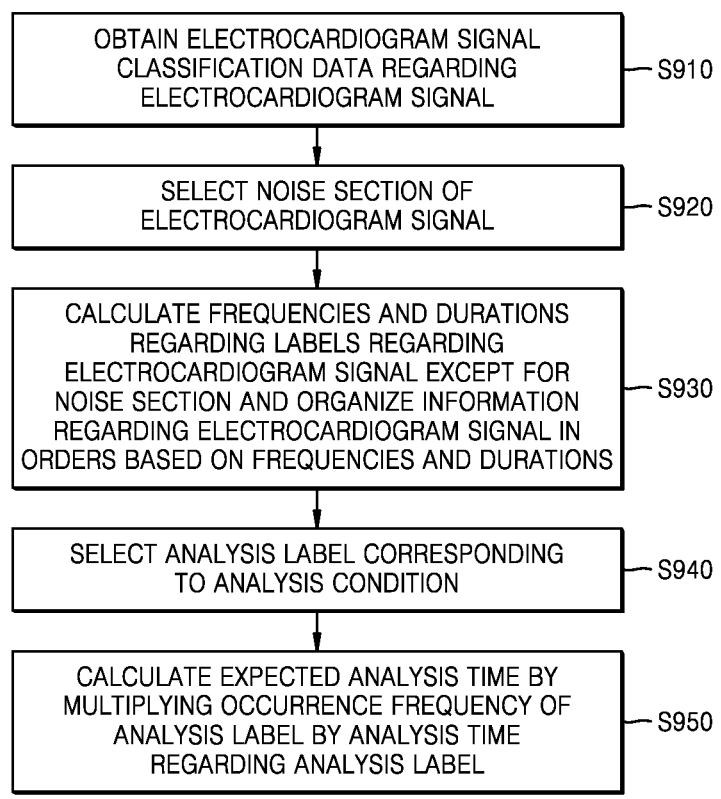
FIG. 13 is a flowchart of a method of analyzing electrocardiogram data according to one or more embodiments.

FIG. 13 is a flowchart of a method of analyzing electrocardiogram data according to one or more embodiments.

In operation S910, the electrocardiogram data processing server 100 may receive an electrocardiogram signal and classification data regarding the electrocardiogram signal.

In operation S920, the electrocardiogram data processing server 100 may select a noise section of the electrocardiogram signal.

In operation S930, the electrocardiogram data processing server 100 may calculate frequencies of labels regarding the electrocardiogram signal except for the noise section and information regarding durations of the labels and organize information regarding the electrocardiogram signal in an order determined based on the frequencies and the durations. Output data implemented such that data regarding sections of the electrocardiogram signal are organized in the order of high frequency, low frequency, long duration, and short duration may be generated.

In operation S940, the electrocardiogram data processing server 100 may select an analysis label corresponding to an analysis condition.

In operation S950, the electrocardiogram data processing server 100 may calculate an expected analysis time by multiplying the number of occurrences of the analysis label by an analysis time regarding the analysis label.

Figure 14:
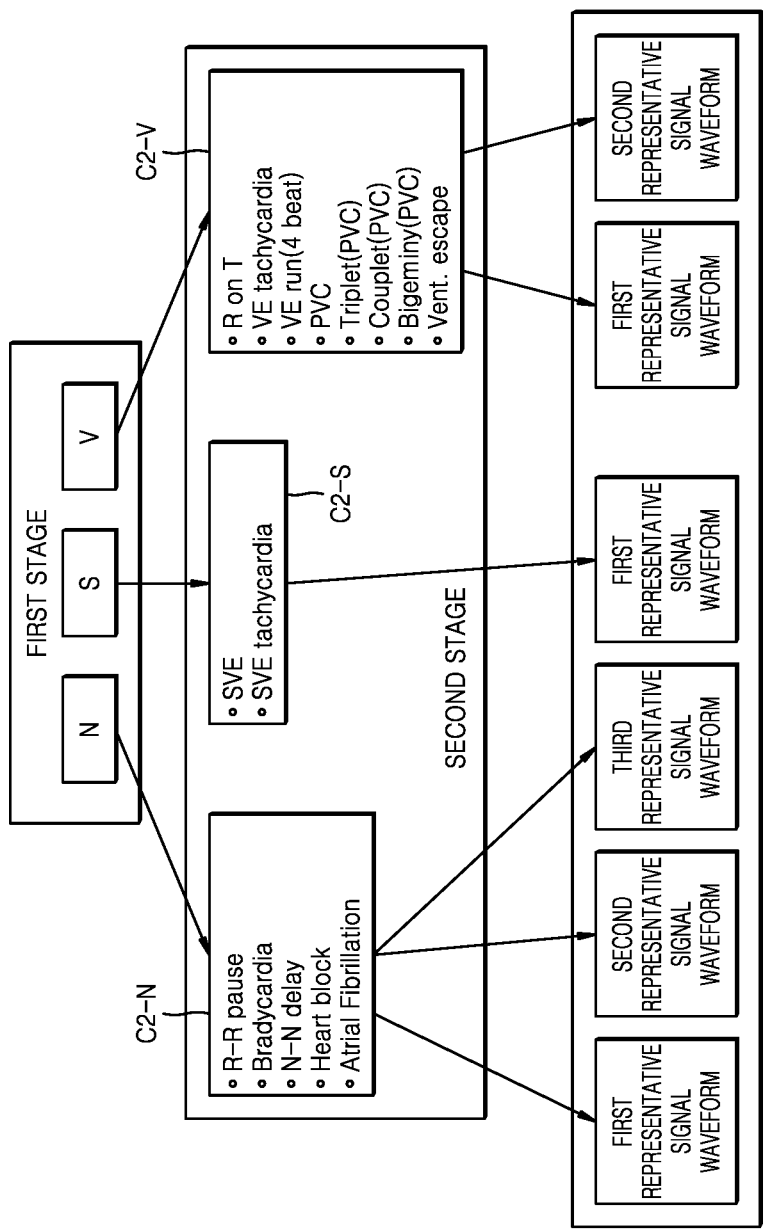
FIG. 14 is a diagram showing an example of labels included in classification data regarding an electrocardiogram signal according to one or more embodiments.

FIG. 14 is a diagram showing an example of labels included in classification data regarding an electrocardiogram signal according to one or more embodiments.

As shown in FIG. 14, classification data regarding an electrocardiogram signal may include labels generated in three stages. In a first stage, an electrocardiogram signal may be classified into category values (labels) including a normal beat N, supraventricular ectopy beat (SVEB) S and ventricular ectopy beat (VEB) V according to a certain classification criterion. Here, the classification criterion may include IEC 60601-2-47, which is an international standard, or KS C IEC 60601-2-47, which is a domestic standard, but is not limited thereto. Also, the classification criteria may be changed or added by a user.

N, S, and V in the first stage may be classified into category values of a second stage, respectively. The category values of N may be reclassified into category values of C2-N. The category values of S may be reclassified into category values of C2-S. The category values of V may be reclassified into category values of C2-V.

According to one or more embodiments, after classifying the electrocardiogram signal based on category values C2-N, C2-S, and C2-V, the electrocardiogram signal may be classified according to representative signal waveforms of the respective categories. For the electrocardiogram signal data stream, signal segments may be classified according to category values and representative signal waveforms belonging to the category values. The category values may each be designed to correspond to a corresponding label.

FIG. 15 is a table showing sections to be analyzed corresponding to analysis conditions.

When labels including a first label AFIB_1 and a second label AFIB_2 are input as analysis conditions by a medical staff, the electrocardiogram data processing server 100 may retrieve sections corresponding to the first label AFIB_1 and sections corresponding to the second label AFIB_2 and retrieve dates of occurrence, occurrence starting time points, durations, occurrence ending time points, etc. regarding corresponding sections. The electrocardiogram data processing server 100 may generate and store retrieved data as a table as shown in FIG. 15. Here, examples of AFIB_1 and AFIB_2 are "NSR-AF-PAUSE-NSR" and "NSR-AF-NSR", respectively.

Figure 16:
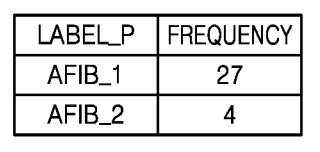
Figure 17:
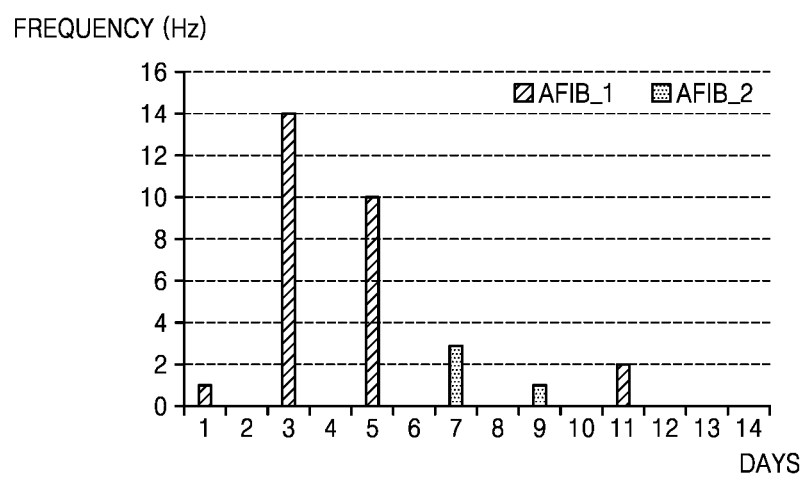
FIG. 17 is a diagram showing daily occurrence frequencies regarding the sections to be analyzed of FIG. 15.

FIG. 16 is a table showing occurrence frequencies of a first label and a second label in the sections to be analyzed of FIG. 15, and FIG. 17 is a graph showing daily occurrence frequencies in day unit regarding the sections to be analyzed of FIG. 15.

The electrocardiogram data processing server 100 may count and store the frequencies of occurrence of sections corresponding to the first label AFIB_1 and the second label AFIB_2. The electrocardiogram data processing server 100 may count and store the daily frequencies of occurrence of sections corresponding to the first label AFIB_1 and the second label AFIB_2. The electrocardiogram data processing server 100 may transmit data regarding the frequencies of occurrence regarding the sections corresponding to the first label AFIB_1 and the second label AFIB_2 to a medical staff terminal, such that the data regarding the frequencies of occurrence is output from the medical staff terminal.

As shown in FIG. 17, in correspondence with a measurement period for 14 days, it may be extracted that the first label AFIB_1 occurs 14 times on a third day and occurs 10 times on a fifth day. It may be extracted that the second label AFIB_2 occurs 3 times on a seventh day. In this regard, daily occurrence frequencies during a measurement period are expressed. It may be retrieved that the first label AFIB_1 occurs most frequently on the third day. The electrocardiogram data processing server 100 may store data regarding the daily occurrence frequencies. The electrocardiogram data processing server 100 may transmit data regarding the daily occurrence frequencies regarding the sections corresponding to the first label AFIB_1 and the second label AFIB_2 to a medical staff terminal, such that the data regarding the daily occurrence frequencies output from the medical staff terminal.

Figure 18:
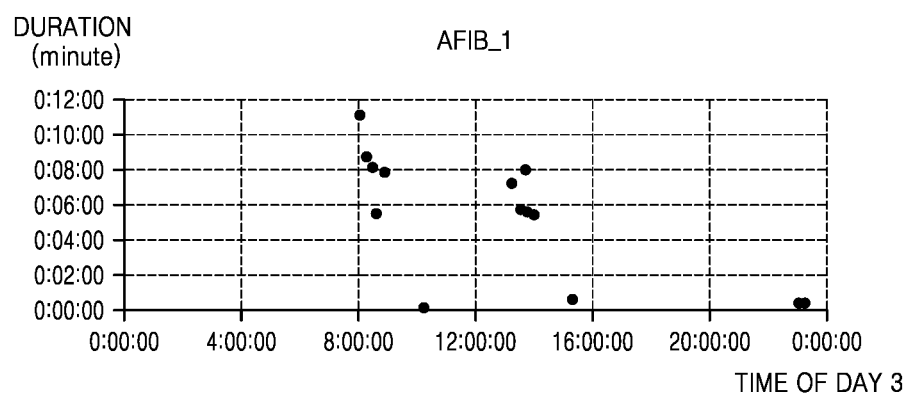
FIG. 18 is a graph showing time points at which the first label of FIG. 16 occurs.

FIG. 18 is a graph showing time points at which the first label AFIB_1 of FIG. 16 occurs.

The electrocardiogram data processing server 100 may generate and store time points at which the first label AFIB_1 occurs in the form of a graph of time and number of times. The electrocardiogram data processing server 100 may transmit the time points at which the first label AFIB_1 occurs to a medical staff terminal in the form of a graph of time and number of times.

Figure 19A:
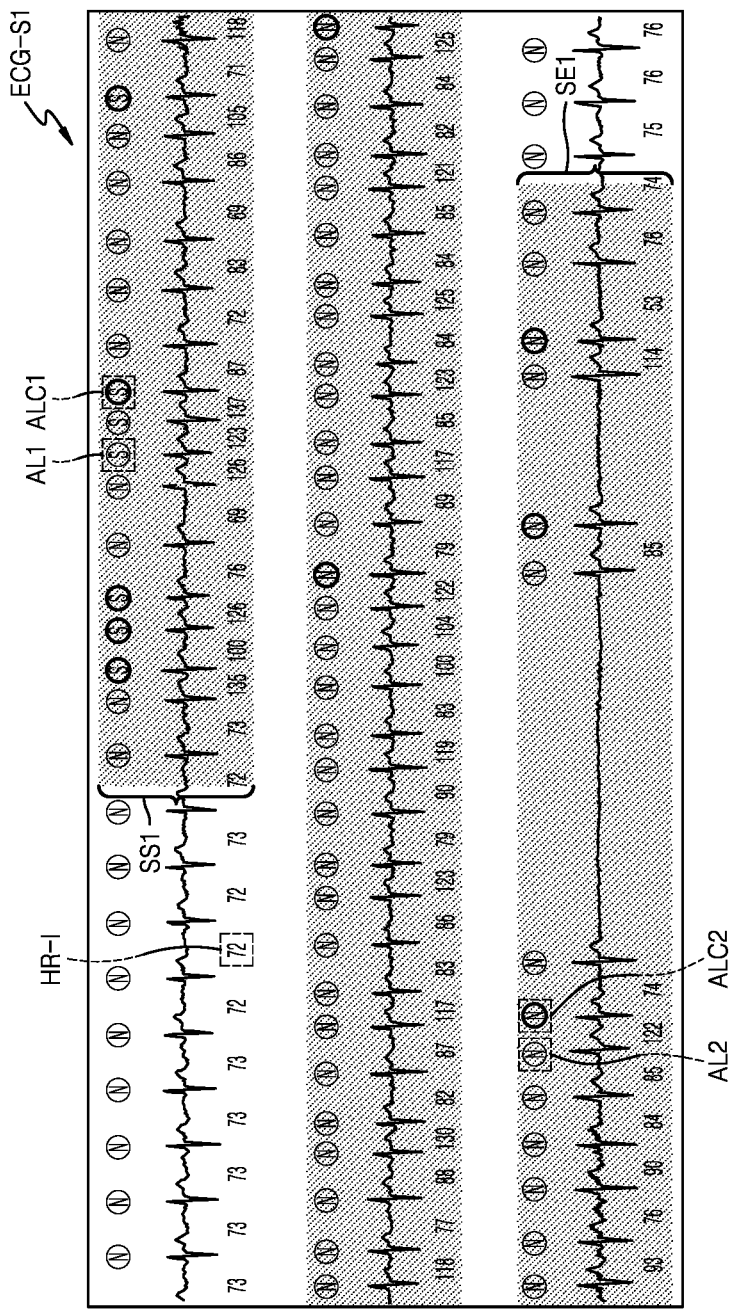
FIG. 19A is a diagram showing an example of first output data including a first electrocardiogram signal and labels.
Figure 19B:
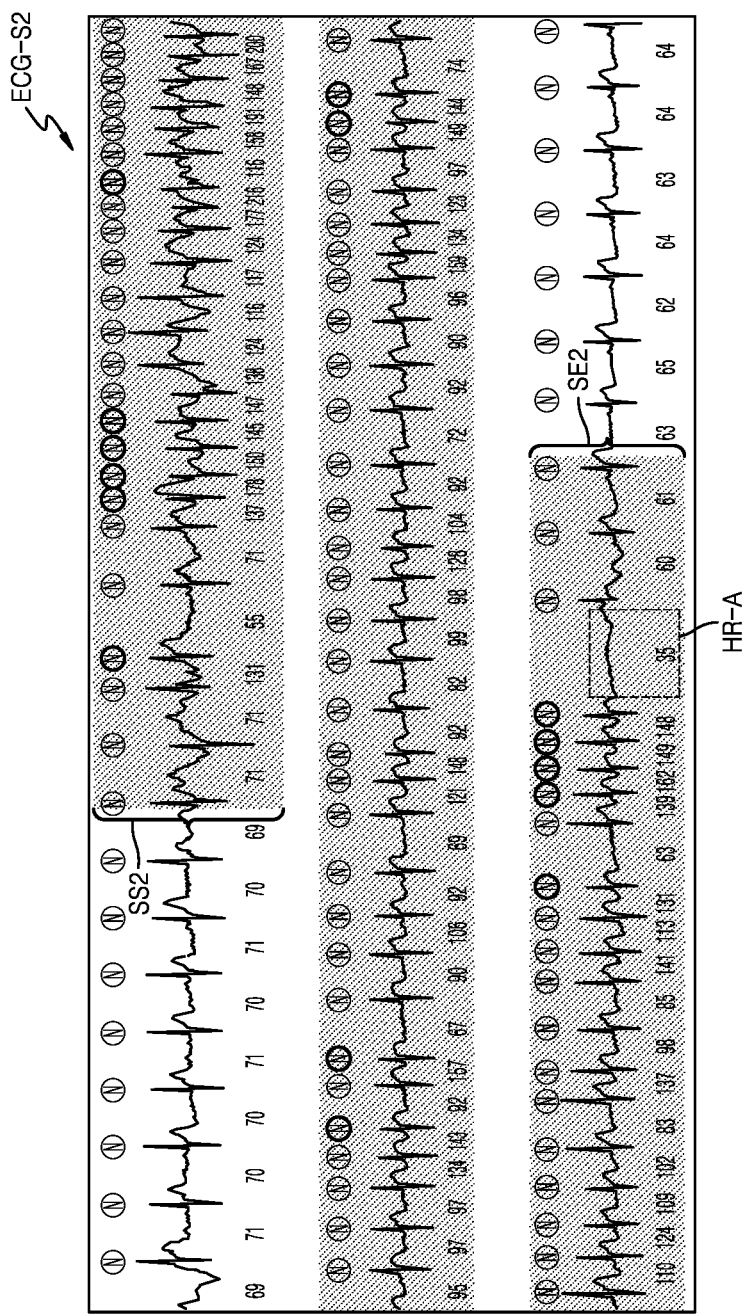
FIG. 19B is a diagram showing an example of second output data including a second electrocardiogram signal and heart rates.

FIG. 19A is a diagram showing an example of first output data including a first electrocardiogram signal and labels. FIG. 19B is a diagram showing an example of second output data including a second electrocardiogram signal and heart rates.

The electrocardiogram data processing server 100 may generate an electrocardiogram signal and output data regarding classification data regarding the electrocardiogram signal as shown in FIG. 19A.

A first signal section SS1 to SE1 of FIG. 19A is a waveform corresponding to AFIB_1 and is a section in which a heart rate deviates starts from a point outside a normal range, fibrillation occurs, and the heart rate returns to the normal range. In the section, there is a section (PAUSE) in which heart rate=0. Classification data ECG-S1 regarding the electrocardiogram signal may include a heart rate HR-I and labels AL1, ALC2, AL2, and ALC2 for a set time interval. Labels generated by an algorithm for generating classification data may be indicated as AL1, AL2, etc. Labels modified by an analyst after being generated may be indicated as ALC1, ALC2, etc. In other words, labels generated by an algorithm and labels modified by an analyst after being generated may be indicated in different forms.

A second time section SS2 to SE2 of FIG. 19B is a time interval corresponding to AFIB_2 and is characterized in that there is no section in which heart rate=0. Although there was a PAUSE label for HR-A included in classification data ECG-S2 regarding the electrocardiogram signal shown in FIG. 19B, since the heart rate was not 0 in a corresponding section, it was determined that the section does not correspond to the PAUSE label.

The apparatus described above may be implemented as a hardware component, a software component, and/or a combination of hardware components and software components. For example, the devices and components described in the embodiments may be implemented by using one or more general purpose or special purpose computers, such as a processor, a controller, an arithmetic logic unit (ALU), a digital signal processor, a microcomputer, a field programmable gate array (FPGA). a programmable logic unit (PLU), a microprocessor, or any other device capable of executing and responding to instructions. A processing device may execute an operating system (OS) and one or more software applications running on the OS. The processing device may also access, store, manipulate, process, and generate data in response to execution of software. For the convenience of explanation, it has been described above that one processing device is used. However, it would be obvious to one of ordinary skill in the art that the processing device may include a plurality of processing elements and/or a plurality of types of processing elements. For example, the processing device may include a plurality of processors or one processor and one controller. Also, other processing configurations like parallel processors may be employed.

The software may include a computer program, code, instructions, or a combination of one or more of the foregoing, to configure the processing device to operate as demanded or to command the processing device independently or collectively. For the purpose of interpreting or providing instructions or data to the processing device, software and/or data may be permanently or temporarily embodied in any type of machine, component, physical device, virtual equipment, computer storage medium, or a signal wave to be transmitted. The software may be distributed over networked computer systems so that they may be stored or executed in a distributed manner. The software and data may be stored on one or more computer-readable recording media.

The methods according to embodiments may be embodied in the form of program instructions that can be executed by various computer means and recorded on a computer readable medium. The computer-readable media may include program instructions, data files, and data structures alone or a combination thereof. The program commands recorded on the medium may be specially designed and configured for example embodiments or may be published and available to one of ordinary skill in computer software. Examples of the computer-readable recording medium include a hardware device specially configured to store and perform program instructions, for example, a magnetic medium, such as a hard disk, a floppy disk, and a magnetic tape, an optical recording medium, such as a CD-ROM, a DVD, and the like, a magneto-optical medium, such as a floptical disc, ROM, RAM, a flash memory, and the like. Examples of program commands include machine language code such as code generated by a compiler, as well as high-level language code that may be executed by a computer using an interpreter or the like. The hardware device described above may be configured to operate as one or more software modules to perform the operations of the embodiments, and vice versa.

Although the embodiments have been described by the limited embodiments and the drawings as described above, various modifications and variations are possible to one of ordinary skill in the art from the above description. For example, the described techniques may be performed in a different order than the described method, and/or components of the described systems, structures, devices, circuits, etc. may be combined or combined in a different manner than the described method, or other components. Or even if replaced or substituted by equivalents, an appropriate result can be achieved.

Therefore, other implementations, other embodiments, and equivalents of the claims fall within the scope of the claims to be described later.

It should be understood that embodiments described herein should be considered in a descriptive sense only and not for purposes of limitation. Descriptions of features or aspects within each embodiment should typically be considered as available for other similar features or aspects in other embodiments. While one or more embodiments have been described with reference to the figures, it will be understood by those of ordinary skill in the art that various changes in form and details may be made therein without departing from the spirit and scope of the disclosure as defined by the following claims.

What is claimed is:

1. A method of generating and processing analysis data regarding electrocardiogram signals of a target object, the method comprising:
receiving, by an electrocardiogram data processing server, an electrocardiogram signal of a target object;
receiving, by the electrocardiogram data processing server, a first classification data regarding the electrocardiogram signal of the target object, wherein the first classification data comprises labels classified according to pre-set category values with respect to the electrocardiogram signal of the target object, and wherein the receiving the first classification data further comprises dividing the electrocardiogram signal into a plurality of signal segments according to signal waveforms and setting each of the signal segments to one of the pre-set category values;
generating, by the electrocardiogram data processing server, statistical data based on a past medical history and symptom information at a time of measurement of the target object using the first classification data, wherein the statistical data includes pattern information regarding the electrocardiogram signal of the target object when the target object feels pain, frequencies of patterns occurring in the electrocardiogram signal, an occurrence period of the patterns, and data regarding the patterns per a predetermined unit period of the electrocardiogram signal, and wherein the symptom information at the time of measurement includes symptom detection information that is input by the target object, questionnaire data in communication with the target object, and past medical history information of the target object; and
generating, by the electrocardiogram data processing server, a second classification data based on the statistical data and the symptom information;

determining, by the electrocardiogram data processing server, a section of interest to be analyzed in the electrocardiogram signal based on the second classification data;

extracting, by the electrocardiogram data processing server, first target signal sections corresponding to the section of interest to be analyzed in the electrocardiogram signal;

calculating, by the electrocardiogram data processing server, an expected analysis time for the first target signal sections corresponding to the section of interest;

upon determination that the expected analysis time is equal to or greater than a pre-set reference value, repeating, by the electrocardiogram data processing server, the generating of the second classification data and the determining of the section of interest to be analyzed, by changing the statistical data and changing the symptom information in order to reduce the expected analysis time to be less than the pre-set reference value;

extracting, by the electrocardiogram data processing server, second target signal sections after the repeated generation of the second classification data and the repeated determination of the section of interest to be analyzed;

determining, by the electrocardiogram data processing server, that the expected analysis time of the second target signal section is less than the pre-set reference value; and upon determination that the expected analysis time of the second target signal sections is less than the pre-set reference value, transmitting, by the electrocardiogram data processing server, to an external terminal, the second target signal sections and the expected analysis time thereof such that analyzing the second target signal sections is performed after the expected analysis time of the second target signal sections is determined to be less than the pre-set reference value.

2. The method of claim 1 further comprising:

receiving, by the electrocardiogram data processing server, a first label for a first signal section via the external terminal;

when label information for the first signal section is not identical to the first label, re-extracting, by the electrocardiogram data processing server, the first signal section among the second target signal sections; and generating, by the electrocardiogram data processing server, a third classification data by re-classifying the first signal section according to the first label; and receiving, by the electrocardiogram data processing server, a first priority value for the first signal section via the external terminal; and wherein the generating the third classification data generating the third classification data by setting the first priority value to the first signal section.

3. The method of claim 2 further comprising:

receiving, by the electrocardiogram data processing server, an abnormal signal marker for the first signal section via the external terminal; and re-classifying, by the electrocardiogram data processing server, the first signal section according to the abnormal signal marker.

4. The method of claim 2 further comprising:

receiving, by the electrocardiogram data processing server, a second priority value for a second label via the external terminal; and re-classifying, by the electrocardiogram data processing server, the second target signal sections according to the second priority value.

5. The method of claim 2 further comprising:

receiving, by the electrocardiogram data processing server, via the external terminal, an input for excluding a second signal section from the section of interest to be analyzed;

transmitting, by the electrocardiogram data processing server, to a medical staff terminal, a confirmation request that the second signal section is excluded; and requesting, by the electrocardiogram data processing server, an approval reply.

6. The method of claim 2, further comprising:

transmitting, by the electrocardiogram data processing server, to a medical staff terminal, a confirmation request that the first label received from the external terminal is applied to the third classification data; and requesting, by the electrocardiogram data processing server, an approval reply.

7. An electrocardiogram data processing server comprising:

a processor;

a computer readable memory storing a computer readable instructions executable by the processor; and a communication unit, wherein the instructions include:

receiving an electrocardiogram signal of a target object via the communication unit, receiving a first classification data regarding the electrocardiogram signal of the target object via the communication unit, wherein the first classification data comprises labels classified according to pre-set category values with respect to the electrocardiogram signal of the target object, and wherein the receiving the first classification data further comprises dividing the electrocardiogram signal into a plurality of signal segments according to signal waveforms and setting each of the signal segments to one of the pre-set category values;

generating statistical data and symptom information at a time of measurement of the target object using the first classification data, wherein the statistical data includes pattern information regarding the electrocardiogram signal of the target object when the target object feels pain, frequencies of patterns occurring in the electrocardiogram signal, an occurrence period of the patterns, and data regarding the patterns per a predetermined unit period of the electrocardiogram signal, and wherein the symptom information at the time of measurement includes symptom detection information that is input by the target object, questionnaire data in communication with the target object, and past medical history information of the target object, generate a second classification data regarding the electrocardiogram signal based on the statistical data and the symptom information, determine a section of interest to be analyzed in the electrocardiogram signal based on the second classification data, extract first target signal sections corresponding to the section of interest to be analyzed in the electrocardiogram signal;

calculate an expected analysis time for the first target signal sections corresponding to the section of interest to be analyzed, upon determination that the expected analysis time of the first target signal sections is equal to or greater than a pre-set reference value, repeating the generating of the second classification data and the determining of the section of interest to be analyzed, by changing the statistical data and changing the symptom information in order to reduce the expected analysis time to be less than the pre-set reference value;

extracting second target signal sections after the repeated generation of the second classification data and the repeated determination of the section of interest to be analyzed;

determining that the expected analysis time of the second target signal sections is less than the pre-set reference value; and upon determination that the expected analysis time of the second target signal sections is less than the pre-set reference value, transmit, to an external terminal, the second target signal sections and the expected analysis time thereof via the communication unit, such that analyzing the second target signal sections is performed after the expected analysis time is determined to be less than the pre-set reference value.

8. The electrocardiogram data processing server of claim 7, wherein the instructions further include:

receiving a first label for a first signal section via the external terminal;

when label information for the first signal section is not identical to the first label, re-extracting the first signal section among the second target signal sections; and generating a third classification data by re-classifying the first signal section according to the first label; and receiving a first priority value for the first signal section via the external terminal, and wherein the generating the third classification data further includes generating the third classification data by setting the first priority value to the first signal section.

9. The electrocardiogram data processing server of claim 8, wherein the instructions further include:

receiving an abnormal signal marker for the first signal section from the external terminal via the communication unit, and re-classifying the second target signal sections according to the abnormal signal marker.

10. The electrocardiogram data processing server of claim 8, wherein the instructions further include:

receiving a second priority value for a second label via the external terminal, and re-classifying the second target signal sections according to the second priority value.

11. The electrocardiogram data processing server of claim 8, wherein the instructions further include:

receiving an input for excluding a second signal section from the external terminal via the communication unit, transmitting, to a medical staff terminal, a confirmation request that the second signal section is excluded, and requesting an approval reply.

12. The electrocardiogram data processing server of claim 8, wherein the instructions further include, via the communication unit:

Transmitting, to a medical staff terminal, a confirmation request that the first label received from the external terminal is applied, and requesting an approval reply.

* * * * *